US011013446B2

(12) United States Patent
Felix et al.

(10) Patent No.: US 11,013,446 B2
(45) Date of Patent: May 25, 2021

(54) SYSTEM FOR SECURE PHYSIOLOGICAL DATA ACQUISITION AND DELIVERY

(71) Applicant: Bardy Diagnostics, Inc., Seattle, WA (US)

(72) Inventors: Jason Felix, Vashon Island, WA (US); Ezra M. Dreisbach, Vashon, WA (US); Jon Mikalson Bishay, Lexington, KY (US); Corey Bailey Williamson, Bellingham, WA (US); Gust H. Bardy, Carnation, WA (US)

(73) Assignee: BARDY DIAGNOSTICS, INC., Seattle, WA (US)

( * ) Notice: Subject to any disclaimer, the term of this patent is extended or adjusted under 35 U.S.C. 154(b) by 0 days.

(21) Appl. No.: 16/593,647

(22) Filed: Oct. 4, 2019

(65) Prior Publication Data
US 2020/0029842 A1    Jan. 30, 2020

Related U.S. Application Data

(63) Continuation of application No. 16/404,228, filed on May 6, 2019, now Pat. No. 10,433,743, which is a (Continued)

(51) Int. Cl.
*A61B 5/366* (2021.01)
*A61B 5/318* (2021.01)
(Continued)

(52) U.S. Cl.
CPC ............ *A61B 5/318* (2021.01); *A61B 5/0006* (2013.01); *A61B 5/0022* (2013.01); *A61B 5/259* (2021.01);
(Continued)

(58) Field of Classification Search
CPC ........ A61B 2560/0487; A61B 2562/08; A61B 5/0006; A61B 5/0022; A61B 5/04017;
(Continued)

(56) References Cited

U.S. PATENT DOCUMENTS 3,215,136 A   11/1965  Holter et al.
3,569,852 A   3/1971   Berkovits
(Continued)

FOREIGN PATENT DOCUMENTS

DE   19955211   5/2001
EP   1859833    11/2007
(Continued)

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).
(Continued)

*Primary Examiner* — George Manuel
(74) *Attorney, Agent, or Firm* — Patrick J. S. Inouye; Leonid Kisselev

(57) ABSTRACT

A system for secure physiological data acquisition and delivery is provided. The system includes a monitoring patch that includes a flexible backing; a pair of electrocardiographic electrodes included on a contact surface of each end of the flexible backing; a receptacle affixed to a non-contacting surface of the flexible backing and including an electro-mechanical docking interface for interfacing with a monitor recorder; a pair of flexible circuit traces affixed at each end of the flexible backing with each circuit trace connecting one of the electrocardiographic electrodes to the electro-mechanical docking interface; and a circuit operable to store an identifier associated with the patch and an encrypted password necessary to access physiological moni-
(Continued)

toring data obtained using the patch identified by that identifier, the circuit configured to provide via the electromechanical docking interface the password and the identifier to the monitor recorder.

20 Claims, 16 Drawing Sheets

Related U.S. Application Data continuation of application No. 15/966,896, filed on Apr. 30, 2018, now Pat. No. 10,278,603, which is a continuation of application No. 15/472,183, filed on Mar. 28, 2017, now Pat. No. 9,955,885, which is a continuation of application No. 14/656,661, filed on Mar. 12, 2015, now Pat. No. 9,619,660, which is a continuation-in-part of application No. 14/341,698, filed on Jul. 25, 2014, now abandoned, which is a continuation-in-part of application No. 14/082,071, filed on Nov. 15, 2013, now Pat. No. 9,433,367, which is a continuation-in-part of application No. 14/080,717, filed on Nov. 14, 2013, now Pat. No. 9,545,204, said application No. 14/082,071 is a continuation-in-part of application No. 14/080,725, filed on Nov. 14, 2013, now Pat. No. 9,730,593, said application No. 14/656,661 is a continuation-in-part of application No. 14/488,230, filed on Sep. 16, 2014, now Pat. No. 9,700,227, which is a continuation-in-part of application No. 14/080,725, filed on Nov. 14, 2013, now Pat. No. 9,730,593.

(60) Provisional application No. 61/882,403, filed on Sep. 25, 2013.

(51) Int. Cl.
| | |
|---|---|
| *G06F 21/60* | (2013.01) |
| *A61B 5/00* | (2006.01) |
| *G06F 21/62* | (2013.01) |
| *G16H 40/63* | (2018.01) |
| *A61B 90/90* | (2016.01) |
| *A61B 90/96* | (2016.01) |
| *A61B 5/259* | (2021.01) |
| *A61B 5/282* | (2021.01) |
| *A61B 5/316* | (2021.01) |
| *A61B 5/333* | (2021.01) |
| *A61B 5/339* | (2021.01) |
| *A61B 5/349* | (2021.01) |
| *A61B 5/361* | (2021.01) |
| *A61B 5/363* | (2021.01) |

(52) U.S. Cl.
CPC .............. *A61B 5/282* (2021.01); *A61B 5/316* (2021.01); *A61B 5/333* (2021.01); *A61B 5/339* (2021.01); *A61B 5/349* (2021.01); *A61B 5/361* (2021.01); *A61B 5/363* (2021.01); *A61B 5/366* (2021.01); *A61B 5/6823* (2013.01); *A61B 5/6832* (2013.01); *A61B 5/6833* (2013.01); *A61B 5/7203* (2013.01); *A61B 5/742* (2013.01); *A61B 5/748* (2013.01); *A61B 90/90* (2016.02); *A61B 90/96* (2016.02); *G06F 21/604* (2013.01); *G06F 21/6218* (2013.01); *G16H 40/63* (2018.01); *A61B 2560/0487* (2013.01); *A61B 2562/08* (2013.01)

(58) Field of Classification Search
CPC .............. A61B 5/0402; A61B 5/04085; A61B 5/04087; A61B 5/0432; A61B 5/044; A61B 5/0452; A61B 5/046; A61B 5/0464; A61B 5/0472; A61B 5/6823; A61B 5/6832; A61B 5/6833; A61B 5/7203; A61B 5/742; A61B 5/748; A61B 90/90; A61B 90/96; G06F 21/604; G06F 21/6218; G16H 40/63

See application file for complete search history.

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bomn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |

(56) References Cited

U.S. PATENT DOCUMENTS

| | | |
|---|---|---|
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,454,708 B1 | 9/2002 | Ferguson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0082867 A1* | 6/2002 | MacCarter ........... A61B 5/0002 705/2 |
| 2002/0103422 A1 | 8/2002 | Harder et al. |

(56) References Cited

U.S. PATENT DOCUMENTS

| | | |
|---|---|---|
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027339 A1 | 1/2008 | Nagai et al. |
| 2008/0051668 A1 | 2/2008 | Bardy |
| 2008/0058661 A1 | 3/2008 | Bardy |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0177168 A1 | 12/2008 | Callahan et al. |
| 2008/0306359 A1 | 12/2008 | Zdeblick et al. |
| 2008/0309481 A1 | 12/2008 | Tanaka et al. |
| 2008/0312522 A1 | 12/2008 | Rowlandson et al. |
| 2009/0012412 A1 | 1/2009 | Wiesel |
| 2009/0012979 A1 | 1/2009 | Bateni et al. |
| 2009/0054737 A1 | 2/2009 | Magar et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1 | 6/2009 | Belalcazar et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |

(56) References Cited

U.S. PATENT DOCUMENTS

| | | |
|---|---|---|
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0231947 A1 | 9/2013 | Shusterman |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0094558 A1 | 4/2015 | Russell |
| 2015/0250422 A1 | 9/2015 | Bay |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0217691 A1 | 7/2016 | Kadobayashi et al. |
| 2016/0235318 A1 | 8/2016 | Sarkar |
| 2019/0021671 A1 | 1/2019 | Kumar et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |

OTHER PUBLICATIONS

Alivecor, URL <http://www.businesswire.com/news/home/20121203005545/en/AliveCor%E2%80%99s-Heart-Monitor-Phone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.)

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

(56) References Cited

OTHER PUBLICATIONS

Lauren Gravitz, "When Your Diet Needs a Band-Aid,"Technology Review, MIT. (May 1, 2009).
Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.
McManus et al., "A Novel Application for the Detection of an Irregular Pulse using an iPhone 4S in Patients with Atrial Fibrillation," vol. 10(3), pp. 315-319 (Mar. 2013.)
Nike+ Fuel Band, URL <http://www.nike.com/us/en_us/c/nikeplus-fuelband> (Web page cached on Jan. 11, 2013.)
P. Libby et al.,"Braunwald's Heart Disease—A Textbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web page cached on Sep. 4, 2013.)
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013.)
Zio Patch System, URL <http://www.irhythmtech.com/zio-solution/zio-system/index.html> (Web page cached on Sep. 8, 2013.)
Saadi et al. "Heart Rhythm Analysis Using ECG Recorded With a Novel Sternum Based Patch Technology—A Pilot Study." Cardiotechnix 2013—Proceedings of the International Congress on Cardiovascular Technologies, Sep. 20, 2013.
Anonymous. "Omegawave Launches Consumer App 2.0 in U.S. "Endurance Sportswire—Endurance Sportswire. Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA-IEEE Medical Technology Conference on Individualized Healthcare. May 22, 2010.
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
https://web.archive.org/web/20130831204020/http://www.biopac.com/research.asp?CatID=37&Main=Software (Aug. 2013).
Adinstruments:ECG Analysis Module for LabChart & PowerLab, 2008.
Biopac Systems, Inc. #AS148-Automated ECG Analysis , Mar. 24, 2006.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].
Seifert, Dan, Samsung dives into fitness wearable with the Gear Fit/ The Verge, URL <http://www.theverge.com/2014/2/24/5440310/samsung-dives-into-fitness-wearables-with-the-gear-fit> (Feb. 24, 2014).
Soper, Taylor, Samsung's new Galaxy S5 flagship phone has fingerprint reader, heart rate monitor, URL <http://www.geekwire.com/2014/samsung-galaxy-s5-fingerprint> (Feb. 24, 2014).
Dolcourt, See the Samsung Galaxy S5's Heart rate monitor in action, URL <http://www.cnet.com/news/see-the-samsung-galaxy-s5s-heart-rate-monitor-in-action> (Feb. 25, 2014).
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Vedapulse UK, Jan. 1, 2014 (Jan. 1, 2014), XP002757887, Retrieved from the Internet: URL:http://www.vedapulseuk.com/diagnostic/ [retrieved on May 19, 2016].
http://www.originlab.com/origin#Data_Exploration 2015.
http://www.gtec.at/Products/Software/g.BSanalyze-Specs-Features (2014).
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.

\* cited by examiner

200

170

280

100

60

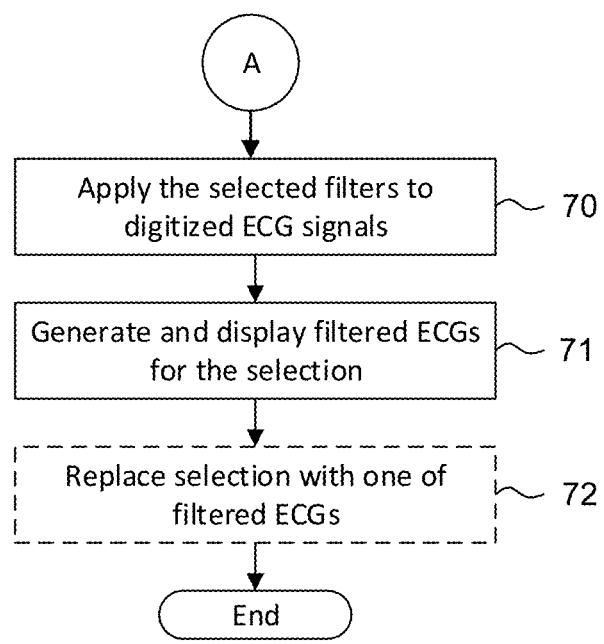
Fig. 18 (Con'd).

SYSTEM FOR SECURE PHYSIOLOGICAL DATA ACQUISITION AND DELIVERY

CROSS-REFERENCE TO RELATED APPLICATION

This non-provisional patent application is a continuation of U.S. Pat. No. 10,433,743, issued Oct. 8, 2019, which is a continuation of U.S. Pat. No. 10,278,603, issued May 7, 2018, which is a continuation of U.S. Pat. No. 9,955,885, issued May 1, 2018, which is a continuation of U.S. Pat. No. 9,619,660, issued Apr. 11, 2017, which is a continuation-in-part of U.S. patent application Ser. No. 14/341,698, filed Jul. 25, 2014, abandoned; which is a continuation-in-part of U.S. Pat. No. 9,433,367, issued Sep. 6, 2016; which is a continuation-in-part of U.S. Pat. No. 9,545,204, issued Jan. 17, 2017, and a continuation-in-part of U.S. Pat. No. 9,730,593, issued Aug. 15, 2017; and which further claims priority under 35 U.S.C. § 119(e) to U.S. Provisional Patent application, Ser. No. 61/882,403, filed Sep. 25, 2013, the disclosures of which are incorporated by reference; the U.S. Pat. No. 9,619,660, issued Apr. 11, 2017, is also a continuation-in-part of U.S. Pat. No. 9,700,227, issued Jul. 11, 2017, which is a continuation-in-part of U.S. Pat. No. 9,730,593, issued Aug. 15, 2017, and further claims priority under 35 U.S.C. § 119(e) to U.S. Provisional Patent application, Ser. No. 61/882,403, filed Sep. 25, 2013, the disclosures of which are incorporated by reference.

FIELD

This application relates in general to electrocardiography and, in particular, to a method for secure physiological data acquisition and storage.

BACKGROUND

The first electrocardiogram (ECG) was invented by a Dutch physiologist, Willem Einthoven, in 1903, who used a string galvanometer to measure the electrical activity of the heart. Generations of physicians around the world have since used ECGs, in various forms, to diagnose heart problems and other potential medical concerns. Although the basic principles underlying Dr. Einthoven's original work, including his naming of various waveform deflections (Einthoven's triangle), are still applicable today, ECG machines have evolved from his original three-lead ECG, to ECGs with unipolar leads connected to a central reference terminal starting in 1934, to augmented unipolar leads beginning in 1942, and finally to the 12-lead ECG standardized by the American Heart Association in 1954 and still in use today. Further advances in portability and computerized interpretation have been made, yet the electronic design of the ECG recording apparatuses has remained fundamentally the same for much of the past 40 years.

Essentially, an ECG measures the electrical signals emitted by the heart as generated by the propagation of the action potentials that trigger depolarization of heart fibers. Physiologically, transmembrane ionic currents are generated within the heart during cardiac activation and recovery sequences. Cardiac depolarization originates high in the right atrium in the sinoatrial (SA) node before spreading leftward towards the left atrium and inferiorly towards the atrioventricular (AV) node. After a delay occasioned by the AV node, the depolarization impulse transits the Bundle of His and moves into the right and left bundle branches and Purkinje fibers to activate the right and left ventricles.

During each cardiac cycle, the ionic currents create an electrical field in and around the heart that can be detected by ECG electrodes placed on the skin. Cardiac electrical activity is then visually represented in an ECG trace by PQRSTU-waveforms. The P-wave represents atrial electrical activity, and the QRSTU components represent ventricular electrical activity. Specifically, a P-wave represents atrial depolarization, which causes atrial contraction.

P-wave analysis based on ECG monitoring is critical to accurate cardiac rhythm diagnosis and focuses on localizing the sites of origin and pathways of arrhythmic conditions. P-wave analysis is also used in the diagnosis of other medical disorders, including imbalance of blood chemistry. Cardiac arrhythmias are defined by the morphology of P-waves and their relationship to QRS intervals. For instance, atrial fibrillation (AF), an abnormally rapid heart rhythm, can be confirmed by the presence of erratic atrial activity or the absence of distinct P-waves and an irregular ventricular rate. Atrial flutter can be diagnosed with characteristic "sawtooth" P-waves often occurring twice for each QRS wave. Some congenital supraventricular tachycardias, like AV node re-entry and atrioventricular reentrant tachycardia using a concealed bypass tract, are characterized by an inverted P-wave occurring shortly after the QRS wave. Similarly, sinoatrial block is characterized by a delay in the onset of P-waves, while junctional rhythm, an abnormal heart rhythm resulting from impulses coming from a locus of tissue in the area of the AV node, usually presents without P-waves or with inverted P-waves within or shortly before or after the QRS wave. Also, the amplitudes of P-waves are valuable for diagnosis. The presence of broad, notched P-waves can indicate left atrial enlargement or disease. Conversely, the presence of tall, peaked P-waves, especially in the initial half, can indicate right atrial enlargement. Finally, P-waves with increased amplitude can indicate hypokalemia, caused by low blood potassium, whereas P-waves with decreased amplitude can indicate hyperkalemia, caused by elevated blood potassium.

Cardiac rhythm disorders may present with lightheadedness, fainting, chest pain, hypoxia, syncope, palpitations, and congestive heart failure (CHF), yet rhythm disorders are often sporadic in occurrence and may not show up in-clinic during a conventional 12-second ECG. Some atrial rhythm disorders, like atrial fibrillation, are known to cause stroke, even when intermittent. Continuous ECG monitoring with P-wave-centric action potential acquisition over an extended period is more apt to capture sporadic cardiac events that can be specifically identified and diagnosed. However, recording sufficient ECG and related physiological data over an extended period remains a significant challenge, despite an over 40-year history of ambulatory ECG monitoring efforts combined with no appreciable improvement in P-wave acquisition techniques since Dr. Einthoven's original pioneering work over a 110 years ago.

Electrocardiographic monitoring over an extended period provides a physician with the kinds of data essential to identifying the underlying cause of sporadic cardiac conditions, especially rhythm disorders, and other physiological events of potential concern. A 30-day observation period is considered the "gold standard" of monitoring by some, yet a 14-day observation period is currently deemed more achievable by conventional ECG monitoring approaches. Realizing a 30-day observation period has proven unworkable with existing ECG monitoring systems, which are arduous to employ; cumbersome, uncomfortable and not user-friendly to the patient; and costly to manufacture and deploy. An intractable problem is the inability to have the monitoring electrodes adhere to the skin for periods of time exceeding 5-14 days, let alone 30 days. Still, if a patient's ECG could be recorded in an ambulatory setting over a prolonged time periods, particularly for more than 14 days, the chances of acquiring meaningful medical information and capturing an abnormal event while the patient is engaged in normal activities are greatly improved.

The location of the atria and their low amplitude, low frequency content electrical signals make P-waves difficult to sense, particularly through ambulatory ECG monitoring. The atria are located either immediately behind the mid sternum (upper anterior right atrium) or posteriorly within the chest (left atrium), and their physical distance from the skin surface, especially when standard ECG monitoring locations are used, adversely affects current strength and signal fidelity. Cardiac electrical potentials measured from the classical dermal locations have an amplitude of only one-percent of the amplitude of transmembrane electrical potentials. The distance between the heart and ECG electrodes reduces the magnitude of electrical potentials in proportion to the square of change in distance, which compounds the problem of sensing low amplitude P-waves. Moreover, the tissues and structures that lie between the activation regions within the heart and the body's surface further attenuate the cardiac electrical field due to changes in the electrical resistivity of adjacent tissues. Thus, surface electrical potentials, when even capable of being accurately detected, are smoothed over in aspect and bear only a general spatial relationship to actual underlying cardiac events, thereby complicating diagnosis. Conventional 12-lead ECGs attempt to compensate for weak P-wave signals by monitoring the heart from multiple perspectives and angles, while conventional ambulatory ECGs primarily focus on monitoring higher amplitude ventricular activity, i.e., the R-wave, that, comparatively, can be readily sensed. Both approaches are relatively unsatisfactory with respect to the P-wave and related need for the accurate acquisition of the P and R-wave medically actionable data of the myriad cardiac rhythm disorders that exist.

Additionally, maintaining continual contact between ECG electrodes and the skin after a day or two of ambulatory ECG monitoring has been a problem. Time, dirt, moisture, and other environmental contaminants, as well as perspiration, skin oil, and dead skin cells from the patient's body, can get between an ECG electrode's non-conductive adhesive and the skin's surface. These factors adversely affect electrode adhesion which in turn adversely affects the quality of cardiac signal recordings. Furthermore, the physical movements of the patient and their clothing impart various compressional, tensile, bending, and torsional forces on the contact point of an ECG electrode, especially over long recording times, and an inflexibly fastened ECG electrode will be prone to becoming dislodged or unattached. Moreover, subtle dislodgment may occur and be unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, multi-week or multi-month monitoring can be performed by implantable ECG monitors, such as the Reveal LINQ insertable cardiac monitor, manufactured by Medtronic, Inc., Minneapolis, Minn. This monitor can detect and record paroxysmal or asymptomatic arrhythmias for up to three years. However, like all forms of implantable medical device (IMD), use of this monitor requires invasive surgical implantation, which significantly increases costs; requires ongoing follow up by a physician throughout the period of implantation; requires specialized equipment to retrieve monitoring data; and carries complications attendant to all surgery, including risks of infection, injury or death. Finally, such devices do not necessarily avoid the problem of signal noise and recording high quality signals.

Holter monitors are widely used for ambulatory ECG monitoring. Typically, they are used for only 24-48 hours. A typical Holter monitor is a wearable and portable version of an ECG that includes cables for each electrode placed on the skin and a separate battery-powered ECG recorder. The leads are placed in the anterior thoracic region in a manner similar to what is done with an in-clinic standard ECG machine using electrode locations that are not specifically intended for optimal P-wave capture but more to identify events in the ventricles by capturing the R-wave. The duration of monitoring depends on the sensing and storage capabilities of the monitor. A "looping" Holter (or event) monitor can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest precludes a patient from replacing or removing the sensing leads and usually involves moving the patient from the physician office to a specialized center within the hospital or clinic.

Noise in recorded signals or other artifacts that do not reflect cardiac activity can contribute to an incorrect diagnosis of a patient. The main sources of noise in an ECG machine are common mode noise, such as 60 Hz power line noise, baseline wander, muscle noise, and radio frequency noise from equipment including pacemakers or other implanted medical devices. Such noise can contribute to an incorrect diagnosis of the patient. For example, electrical or mechanical artifacts, such as produced by poor electrode contact or tremors, can simulate life-threatening arrhythmias. Similarly, baseline wander produced by excessive body motion during an ECG procedure may simulate an ST segment shift ordinarily seen in myocardial ischemia or injury.

Current ECG over-reading software generally does not allow a user to apply an arbitrary noise filter of choice to an ECG trace; users are generally limited to a set of proprietary filters. In addition, conventional over-reading software generally fails to provide users with a way to compare the results of combinations of arbitrary noise filters, thus preventing the user from finding the most appropriate filter. This is especially relevant when trying to record the P-wave or cardiac atrial signal. Further, the interpretation of the ECG is conventionally left entirely to the user, such as a technician or a doctor, and the speed with which a patient can receive some interpretation results of his or her ECG depends entirely on when the user can get to that patient's ECG and how much time the interpretation consumes. In an environment where medical personnel resources are scarce, the interpretation may take an excessively long time.

Further, in addition to ECG signal acquisition and processing, significant challenges exist in regards to the storage of the results of acquisition and processing and making such results quickly available to only authorized parties, such as the patient or the patient's physician. Multiple laws govern the safeguarding of electronic patient records. For example, in the United States, the governing law includes Health Insurance Portability and Accountability Act (HIPAA) while in the European Union the law includes the European Union's Data Protection Directive. In particular, such laws, and HIPAA in particular, focus protection on individually identifiable health information, information that can be tied to a particular patient. Such patient identifying information can include information on the patient's physical or mental health, provision of care to the patient, payment for provision of health care, and identifying information such as name, address, birth date, and social security number. Disclosure of such information in breach of the applicable laws can incur significant penalties. Considering that the disclosure can happen through ways as diverse as a hack of a database containing the records, personnel error, and loss of access information for the database, significant potential for an illegal disclosure exists with conventional record storage techniques.

Therefore, a need remains for a way to facilitate real-time, interactive processing of an ECG.

An additional need exists to accelerate ECG over-reading.

A still further need remains for a way to securely store and provide access to results of ECG analyses and other identifying information.

A further need remains for a low cost extended wear continuously recording ECG monitor attuned to capturing low amplitude cardiac action potential propagation for arrhythmia diagnosis, particularly atrial activation P-waves, and practicably capable of being worn for a long period of time, especially in patient's whose breast anatomy or size can interfere with signal quality in both women and men.

SUMMARY

An ECG is displayed to a user, and a user selection of a desired portion of the ECG is received. A list of filters is provided to the user, and the user can try applying different filters to the selection by selecting of one or more sets of the filters in the list. For each of the sets, the filters are applied to digitized signals corresponding to the selection, a filtered ECG for the selection is generated based on the signals filtered by each of the sets, and the filtered selection ECG traces are displayed to the user. The filtered selections can be displayed side-by-side, allowing the user to compare the ECG traces of the selection filtered using the different sets of filters, and to decide whether application of certain filters resulted in an easily-interpretable ECG, or whether different filters need to be applied. As the result, the user can select the most appropriate filters for the selection, which facilitates removal of noise and enhancement of ECG features that were corrupted by noise or were made difficult to see due to the amplitude of the noise. In addition, by applying the filters to only a particular selection, the user is permitted to filter the selection without degrading the quality of other portions of the ECG.

Physiological monitoring can be provided through a lightweight wearable monitor that includes two components, a flexible extended wear electrode patch and a reusable monitor recorder that removably snaps into a receptacle on the electrode patch. The wearable monitor sits centrally (in the midline) on the patient's chest along the sternum oriented top-to-bottom. The ECG electrodes on the electrode patch are tailored to be positioned axially along the midline of the sternum for capturing action potential propagation in an orientation that corresponds to the aVF lead used in a conventional 12-lead ECG that is used to sense positive or upright P-waves. The placement of the wearable monitor in a location at the sternal midline (or immediately to either side of the sternum), with its unique narrow "hourglass"-like shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms.

Moreover, the electrocardiography monitor offers superior patient comfort, convenience and user-friendliness. The electrode patch is specifically designed for ease of use by a patient (or caregiver); assistance by professional medical personnel is not required. The patient is free to replace the electrode patch at any time and need not wait for a doctor's appointment to have a new electrode patch placed. Patients can easily be taught to find the familiar physical landmarks on the body necessary for proper placement of the electrode patch. Empowering patients with the knowledge to place the electrode patch in the right place ensures that the ECG electrodes will be correctly positioned on the skin, no matter the number of times that the electrode patch is replaced. In addition, the monitor recorder operates automatically and the patient only need snap the monitor recorder into place on the electrode patch to initiate ECG monitoring. Thus, the synergistic combination of the electrode patch and monitor recorder makes the use of the electrocardiography monitor a reliable and virtually foolproof way to monitor a patient's ECG and physiology for an extended, or even open-ended, period of time.

The electrode patch can store an identifier, such as a serial number, and a password associated with the identifier. The password can include a cryptographic hash of the identifier. The password and the identifier are coupled to the data collected using the patch and the data can be stored as electronic medical records (EMR) in a database based on the identifier, with the database storing no patient identifying information. In a further embodiment, information needed to send an alert to a patient or another authorized party, such as a patient's doctor can be stored in the database. A patient or another authorized party can access the data using the identifier and the password. The EMRs can also include results of analysis of data received from the monitor, such as an automated over-read of an ECG trace based on the received data.

In one embodiment, a system for secure physiological data acquisition and delivery is provided. The system includes a monitoring patch that includes a flexible backing including stretchable material defined as an elongated strip with a narrow longitudinal midsection; a pair of electrocardiographic electrodes included on a contact surface of each end of the flexible backing, each electrocardiographic electrode conductively exposed for dermal adhesion and adapted to be positioned axially along a midline of a sternum for capturing action potential propagation; a receptacle affixed to a non-contacting surface of the flexible backing and including an electro-mechanical docking interface for interfacing with a monitor recorder; a pair of flexible circuit traces affixed at each end of the flexible backing with each circuit trace connecting one of the electrocardiographic electrodes to the electro-mechanical docking interface; and a circuit operable to store an identifier associated with the patch and an encrypted password necessary to access physiological monitoring data obtained using the patch identified by that identifier, the circuit configured to provide via the electro-mechanical docking interface the password and the identifier to the monitor recorder.

In a further embodiment, a multipart system for secure physiological data acquisition and delivery is provided. The system includes a monitoring patch that includes a flexible backing including stretchable material defined as an elongated strip; a pair of electrocardiographic electrodes included on a contact surface of each end of the flexible backing, each electrocardiographic electrode conductively exposed for dermal adhesion and adapted to be positioned axially along a midline of a sternum for capturing action potential propagation; a receptacle affixed to a non-contacting surface of the flexible backing and including an electro-mechanical docking interface for interfacing with a monitor recorder, the electro-mechanical docking interface including a plurality of electrical contact mating pads; a pair of flexible circuit traces affixed at each end of the flexible backing with each circuit trace connecting one of the electrocardiographic electrodes to two of the electrical contact mating pads of the electro-mechanical docking interface; and a circuit operable to store an identifier associated with the patch and an encrypted password necessary to access physiological monitoring data obtained using the patch identified by that identifier, the circuit configured to provide via at the electro-mechanical docking interface the password and the identifier to the monitor recorder.

The foregoing aspects enhance ECG monitoring performance and quality by facilitating long-term ECG recording, which is critical to accurate arrhythmia and cardiac rhythm disorder diagnoses.

Providing a real-time, interactive ECG processing apparatus and method for a user, such as a cardiologist or a trained technician, to select and apply ECG noise filters to a desired portion of an ECG trace, particularly but not exclusively the P-wave, simplifies ECG result processing and improves ECG interpretation accuracy.

The monitoring patch is especially suited to the female anatomy, although also easily used over the male sternum. The narrow longitudinal midsection can fit nicely within the inter-mammary cleft of the breasts without inducing discomfort, whereas conventional patch electrodes are wide and, if adhered between the breasts, would cause chafing, irritation, discomfort, and annoyance, leading to low patient compliance.

In addition, the foregoing aspects enhance comfort in women (and certain men), but not irritation of the breasts, by placing the monitoring patch in the best location possible for optimizing the recording of cardiac signals from the atrium, particularly P-waves, which is another feature critical to proper arrhythmia and cardiac rhythm disorder diagnoses.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1:
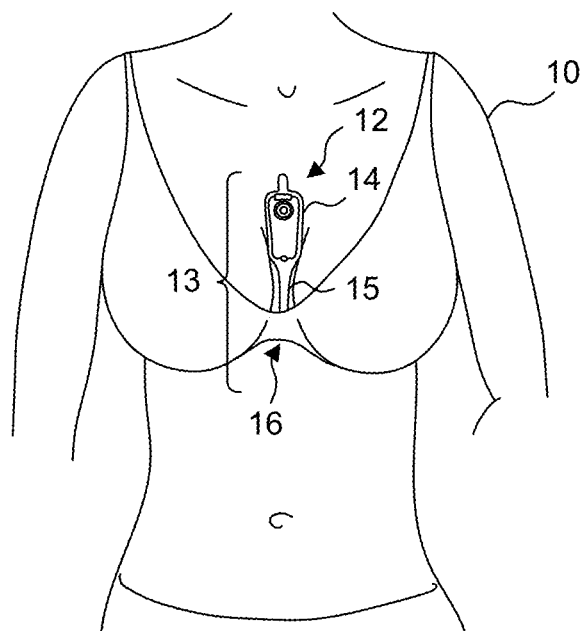
FIGS. 1 and 2 are diagrams showing, by way of examples, an extended wear electrocardiography monitor, including an extended wear electrode patch, respectively fitted to the sternal regions of a female patient and a male patient.
Figure 2:
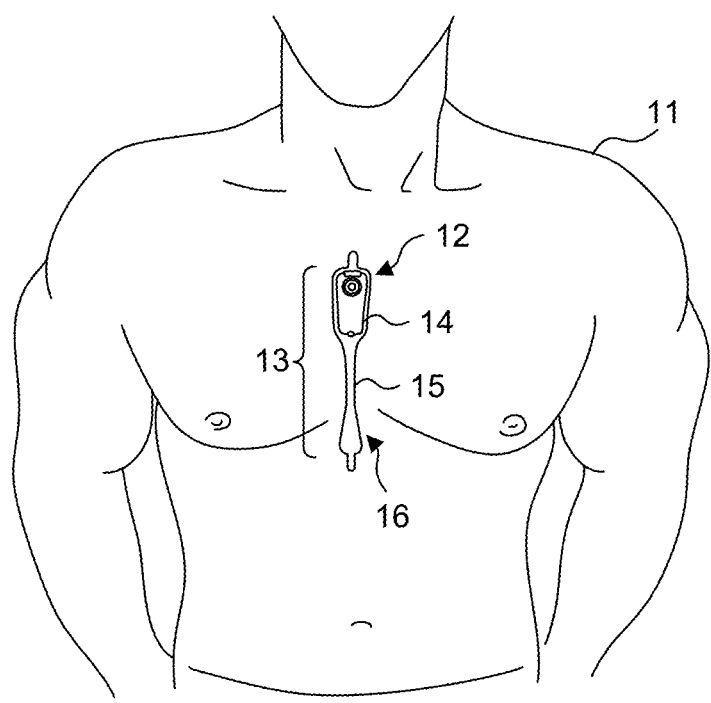

Physiological monitoring can be provided through a wearable monitor that includes two components, a flexible extended wear electrode patch and a removable reusable monitor recorder. Both the electrode patch and the monitor recorder are optimized to capture electrical signals from the propagation of low amplitude, relatively low frequency content cardiac action potentials, particularly the P-waves generated during atrial activation. FIGS. 1 and 2 are diagrams showing, by way of example, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

During ECG monitoring, the amplitude and strength of action potentials sensed on the body's surface are affected to varying degrees by cardiac, cellular, extracellular, vector of current flow, and physical factors, like obesity, dermatitis, large breasts, and high impedance skin, as can occur in dark-skinned individuals. Sensing along the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity by countering some of the effects of these factors.

Figure 3:
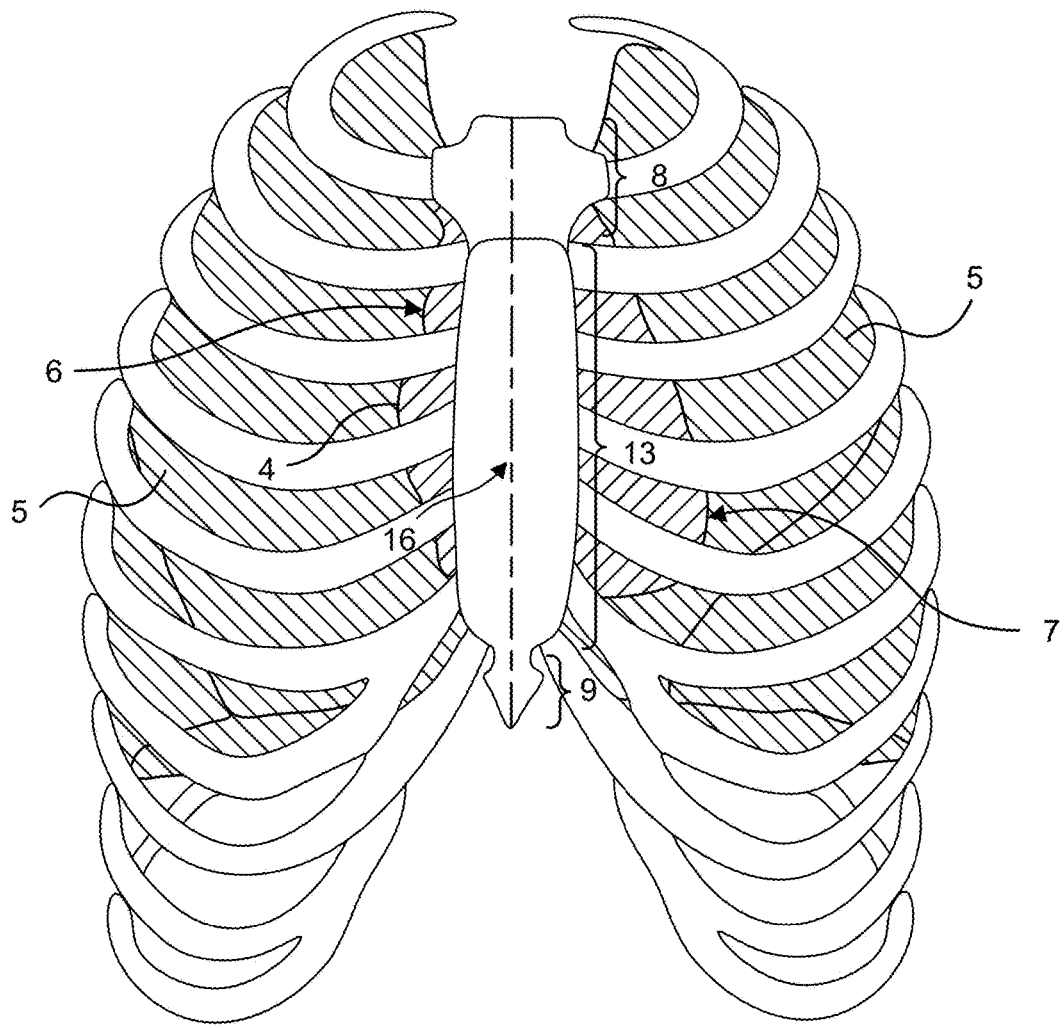
FIG. 3 is a front anatomical view showing, by way of illustration, the locations of the heart and lungs within the rib cage of an adult human.

The ability to sense low amplitude, low frequency content body surface potentials is directly related to the location of ECG electrodes on the skin's surface and the ability of the sensing circuitry to capture these electrical signals. FIG. 3 is a front anatomical view showing, by way of illustration, the locations of the heart 4 and lungs 5 within the rib cage of an adult human. Depending upon their placement locations on the chest, ECG electrodes may be separated from activation regions within the heart 4 by differing combinations of internal tissues and body structures, including heart muscle, intracardiac blood, the pericardium, intrathoracic blood and fluids, the lungs 5, skeletal muscle, bone structure, subcutaneous fat, and the skin, plus any contaminants present between the skin's surface and electrode signal pickups. The degree of amplitude degradation of cardiac transmembrane potentials increases with the number of tissue boundaries between the heart 4 and the skin's surface that are encountered. The cardiac electrical field is degraded each time the transmembrane potentials encounter a physical boundary separating adjoining tissues due to differences in the respective tissues' electrical resistances. In addition, other non-spatial factors, such as pericardial effusion, emphysema or fluid accumulation in the lungs, as further explained infra, can further degrade body surface potentials.

Internal tissues and body structures can adversely affect the current strength and signal fidelity of all body surface potentials, yet low amplitude cardiac action potentials, particularly the P-wave with a normative amplitude of less than 0.25 microvolts (mV) and a normative duration of less than 120 milliseconds (ms), are most apt to be negatively impacted. The atria 6 are generally located posteriorly within the thoracic cavity (with the exception of the anterior right atrium and right atrial appendage), and, physically, the left atrium constitutes the portion of the heart 4 furthest away from the surface of the skin on the anterior chest. Conversely, the ventricles 7, which generate larger amplitude signals, generally are located anteriorly with the anterior right ventricle and most of the left ventricle situated relatively close to the skin surface on the anterior chest, which contributes to the relatively stronger amplitudes of ventricular waveforms. Thus, the quality of P-waves (and other already-low amplitude action potential signals) is more susceptible to weakening from intervening tissues and structures than the waveforms associated with ventricular activation.

The importance of the positioning of ECG electrodes along the sternal midline 15 has largely been overlooked by conventional approaches to ECG monitoring, in part due to the inability of their sensing circuitry to reliably detect low amplitude, low frequency content electrical signals, particularly in P-waves. In turn, that inability to keenly sense P-waves has motivated ECG electrode placement in other non-sternal midline thoracic locations, where the QRSTU components of the ECG that represent ventricular electrical activity are more readily detectable by their sensing circuitry than P-waves. In addition, ECG electrode placement along the sternal midline 15 presents major patient wearability challenges, such as fitting a monitoring ensemble within the narrow confines of the inter-mammary cleft between the breasts, that to large extent drive physical packaging concerns, which can be incompatible with ECG monitors intended for placement, say, in the upper pectoral region or other non-sternal midline thoracic locations. In contrast, the wearable monitor 12 uses an electrode patch 15 that is specifically intended for extended wear placement in a location at the sternal midline 16 (or immediately to either side of the sternum 13). When combined with a monitor recorder 14 that uses sensing circuitry optimized to preserve the characteristics of low amplitude cardiac action potentials, especially those signals from the atria, as further described infra with reference to FIG. 13, the electrode patch 15 helps to significantly improve atrial activation (P-wave) sensing through placement in a body location that robustly minimizes the effects of tissue and body structure.

Referring back to FIGS. 1 and 2, the placement of the wearable monitor 12 in the region of the sternal midline 13 puts the ECG electrodes of the electrode patch 15 in locations better adapted to sensing and recording low amplitude cardiac action potentials during atrial propagation (P-wave signals) than placement in other locations, such as the upper left pectoral region, as commonly seen in most conventional ambulatory ECG monitors. The sternum 13 overlies the right atrium of the heart 4. As a result, action potential signals have to travel through fewer layers of tissue and structure to reach the ECG electrodes of the electrode patch 15 on the body's surface along the sternal midline 13 when compared to other monitoring locations, a distinction that is of critical importance when capturing low frequency content electrical signals, such as P-waves.

Moreover, cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the AV node. The ECG electrodes of the electrode patch 15 are placed with the upper or superior pole (ECG electrode) along the sternal midline 13 beneath the manubrium and the lower or inferior pole (ECG electrode) along the sternal midline 13 in the region of the Xiphoid process 9 and lower sternum. The ECG electrodes are placed primarily in a head-to-foot orientation along the sternum 13 that corresponds to the head-to-foot waveform vector exhibited during atrial activation. This orientation corresponds to the aVF lead used in a conventional 12-lead ECG that is used to sense positive or upright P-waves.

Furthermore, the thoracic region underlying the sternum 13 along the midline 16 between the manubrium 8 and Xiphoid process 9 is relatively free of lung tissue, musculature, and other internal body structures that could occlude the electrical signal path between the heart 4, particularly the atria, and ECG electrodes placed on the surface of the skin. Fewer obstructions means that cardiac electrical potentials encounter fewer boundaries between different tissues. As a result, when compared to other thoracic ECG sensing locations, the cardiac electrical field is less altered when sensed dermally along the sternal midline 13. As well, the proximity of the sternal midline 16 to the ventricles 7 facilitates sensing of right ventricular activity and provides superior recordation of the QRS interval, again, in part due to the relatively clear electrical path between the heart 4 and the skin surface.

Finally, non-spatial factors can affect transmembrane action potential shape and conductivity. For instance, myocardial ischemia, an acute cardiac condition, can cause a transient increase in blood perfusion in the lungs 5. The perfused blood can significantly increase electrical resistance across the lungs 5 and therefore degrade transmission of the cardiac electrical field to the skin's surface. However, the placement of the wearable monitor 12 along the sternal midline 16 in the inter-mammary cleft between the breasts is relatively resilient to the adverse effects to cardiac action potential degradation caused by ischemic conditions as the body surface potentials from a location relatively clear of underlying lung tissue and fat help compensate for the loss of signal amplitude and content. The monitor recorder 14 is thus able to record the P-wave morphology that may be compromised by myocardial ischemia and therefore make diagnosis of the specific arrhythmias that can be associated with myocardial ischemia more difficult.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity, while simultaneously facilitating comfortable long-term wear for many weeks. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the Xiphoid process facilitates sensing of ventricular activity and provides excellent recordation of the QRS interval as the Xiphoid process overlies the apical region of the ventricles.

Figure 4:
FIG. 4 is a diagram showing a monitor patch label that can be used to access results of physiological monitoring, in accordance with one embodiment.

At least one component of the monitor 12 can be associated with at an identifier, such as a serial number, though other kinds of numerical, alphabetical, and alphanumerical identifiers are also possible. Still other kinds of identifiers are also possible. As described below, the identifiers of the patch are associated with results of the monitoring performed using that patch 15 and are used to store and access the results. FIG. 4 is a diagram showing a monitor patch label 200 that can be used to access results of physiological monitoring, in accordance with one embodiment. The label can be given to a patient and other authorized parties upon a dispatch of the monitor 12 to the patient. The label 200 includes the identifier 201 associated with at least one component of the monitor 12. For example, as described further below, the identifier 201 can be encoded on the patch 15 and combined with the data collected by the monitor recorder 14 through the patch 15. Thus, if multiple patches 15 are dispensed to the patient, multiple labels 200 with multiple identifiers 201 will be issued to the patient 10, 11 and other authorized parties. As the patches 15 do not get reused after a monitoring, the monitoring results of different patients will have different identifiers 201 associated with them even if they were obtained using the same monitor recorder 14. While the identifier 201 is shown to have eight components with reference to FIG. 4, other numbers of components are possible.

The label 200 further includes a password 202, also referred to as an access token 202 in the description below, that is also necessary to access the monitoring results. The password 202 can be based on the identifier 202 associated with the patch 15. For example, the password 202 can include a cryptographic hash of at least a portion of the identifier 201 combined with other digits or numbers. The encryption of the identifier 201 can be performed using any suitable encryption hashing function, such as MD5, though other kinds of functions can also be used. In one embodiment, only a portion of the identifier 201, such as 2-3 bytes, are used to create the hash. In a further embodiment, the entire identifier 201 is used to create the hash. The numbers with which the hash can be combined to generate the password can be pseudorandomly generated numbers, though other kinds of numbers are possible. Other kinds of passwords 202 are possible. In one embodiment, the password 202 can be composed of 10 digits; other numbers of digits are possible. Still other kinds of the passwords 202 are possible.

The label 200 further includes a website address 203, such as a url, that the party in possession of the label 200 can use to access the Electronic Medical Records (EMR) that include the monitoring results and other data related to the results, as further described below. With all three pieces of information on the label 201, the patient 10, 11 or another authorized party could visit the web site identified by the address 203, and after entering the identifier 201 and the password 202, access the website EMRs, as further described below with reference to FIGURE X.

To simplify and accelerate accessing the website, the label can further include a barcode 204 that has encoded the identifier 201, the password 202, and the website address 203. In one embodiment, the barcode 204 can be a QR code, though other kinds of barcodes are possible. After scanning the barcode with a device that includes appropriate barcode recognition software, such as a mobile phone or a separate scanner connected to another computing device, the device with would enter the identifier 201 and the password 202 into the website identified by the address 203 and present to the patient the webpage that includes the patient's medical records.

Figure 5:
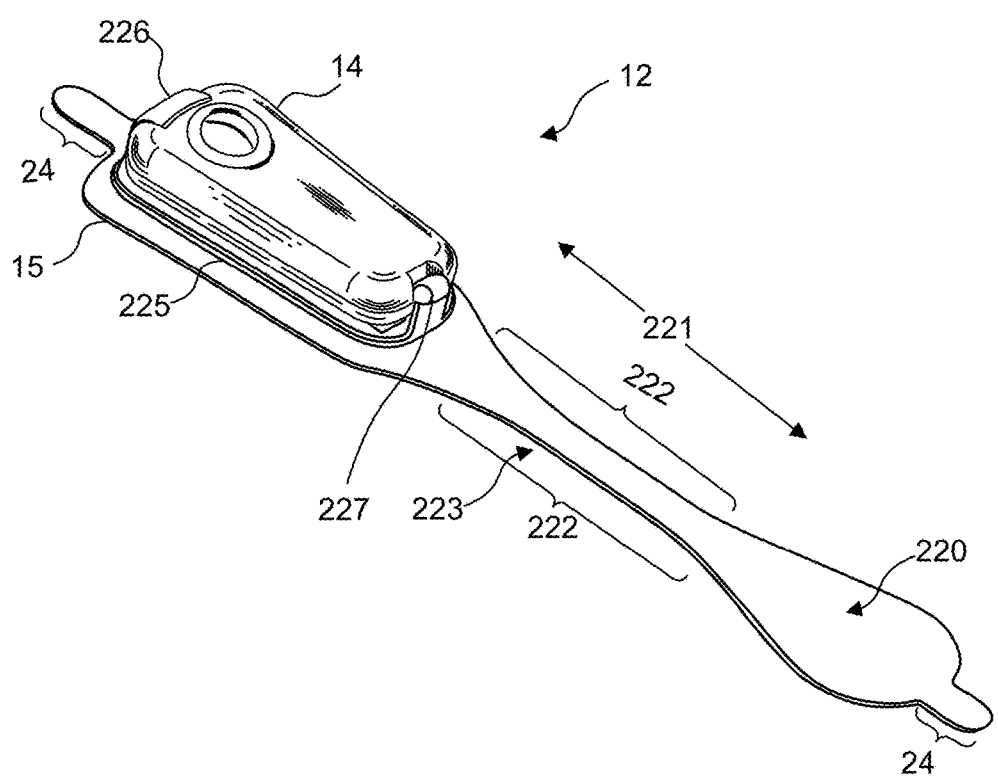
FIG. 5 is a perspective view showing an extended wear electrode patch with a monitor recorder inserted.

The identifier 201 and the password 202 are also included with the data collected by the monitor 12. During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 5 is a perspective view showing an extended wear electrode patch 15 with a monitor recorder 14 in accordance with one embodiment inserted. The body of the electrode patch 15 is preferably constructed using a flexible backing 220 formed as an elongated strip 221 of wrap knit or similar stretchable material with a narrow longitudinal mid-section 223 evenly tapering inward from both sides. A pair of cut-outs 222 between the distal and proximal ends of the electrode patch 15 create a narrow longitudinal midsection 223 or "isthmus" and defines an elongated "hourglass"-like shape, when viewed from above. The upper part of the "hourglass" is sized to allow an electrically non-conductive receptacle 225, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile (but still rounded and tapered to fit comfortably between the breasts) than the lower part of the "hourglass," which is sized primarily to allow just the placement of an ECG electrode of appropriate shape and surface area to record the P-wave and the QRS signals sufficiently given the inter-electrode spacing.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Pat. No. 9,545,204, issued Jan. 17, 2017, the disclosure of which is incorporated by reference. In addition, the cut-outs 222 and longitudinal midsection 223 help minimize interference with and discomfort to breast tissue, particularly in women (and gynecomastic men). The cut-outs 222 and longitudinal midsection 223 further allow better conformity of the electrode patch 15 to sternal bowing and to the narrow isthmus of flat skin that can occur along the bottom of the intermammary cleft between the breasts, especially in buxom women. The cut-outs 222 and longitudinal midsection 223 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 225 during use. The monitor recorder 14 contains electronic circuitry for recording and storing the patient's electrocardiography as sensed via a pair of ECG electrodes provided on the electrode patch 15, such as described in commonly-assigned U.S. Pat. No. 9,730,593, issued Aug. 15, 2018, the disclosure which is incorporated by reference. The non-conductive receptacle 225 is provided on the top surface of the flexible backing 220 with a retention catch 226 and tension clip 227 molded into the non-conductive receptacle 225 to conformably receive and securely hold the monitor recorder 14 in place.

Figure 6:
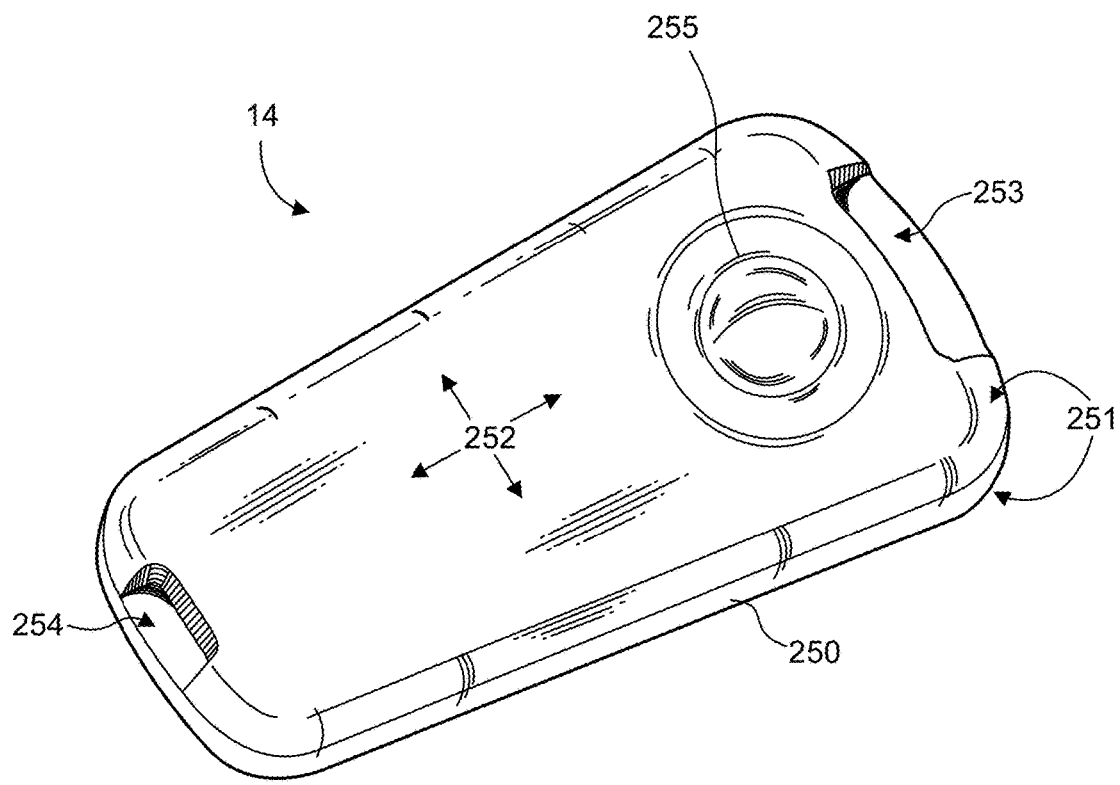
FIG. 6 is a perspective view showing the monitor recorder of FIG. 5.

The monitor recorder 14 includes a sealed housing that snaps into place in the non-conductive receptacle 225. FIG. 6 is a perspective view showing the monitor recorder 14 of FIG. 5. The sealed housing 250 of the monitor recorder 14 intentionally has a rounded isosceles trapezoidal-like shape 252, when viewed from above, such as described in commonly-assigned U.S. Design Pat. No. D717,955, issued Nov. 18, 2014, the disclosure of which is incorporated by reference. In addition, a label, barcode, QR code, or other visible or electronic indicia, such as the identifier 201, is printed on the outside of, applied to the outside of, or integrated into the sealed housing 250 to uniquely identify the monitor recorder 14 and can include a serial number, manufacturing lot number, date of manufacture, and so forth. The edges 251 along the top and bottom surfaces are rounded for patient comfort. The sealed housing 250 is approximately 47 mm long, 23 mm wide at the widest point, and 7 mm high, excluding a patient-operable tactile-feedback button 255. The sealed housing 250 can be molded out of polycarbonate, ABS, or an alloy of those two materials. The button 255 is waterproof and the button's top outer surface is molded silicon rubber or similar soft pliable material. A retention detent 253 and tension detent 254 are molded along the edges of the top surface of the housing 250 to respectively engage the retention catch 226 and the tension clip 227 molded into non-conductive receptacle 225. Other shapes, features, and conformities of the sealed housing 250 are possible.

As mentioned above, the electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 7:
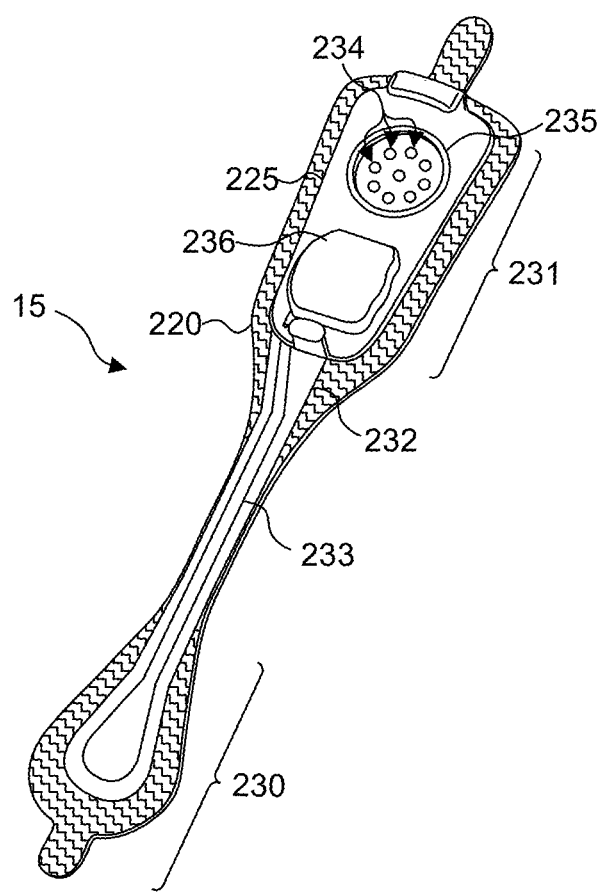
FIG. 7 is a perspective view showing the extended wear electrode patch of FIG. 5 without a monitor recorder inserted.

During use, the electrode patch 15 is first adhered to the skin in the sternal region. FIG. 7 is a perspective view showing the extended wear electrode patch 15 of FIG. 5 without a monitor recorder 14 inserted. A flexible circuit 232 is adhered to each end of the flexible backing 20. A distal circuit trace 233 and a proximal circuit trace (not shown) electrically couple ECG electrodes (not shown) to a pair of electrical pads 234. The electrical pads 234 are provided within a moisture-resistant seal 235 formed on the bottom surface of the non-conductive receptacle 225. When the monitor recorder 14 is securely received into the non-conductive receptacle 225, that is, snapped into place, the electrical pads 234 interface to electrical contacts (not shown) protruding from the bottom surface of the monitor recorder 14, and the moisture-resistant seal 235 enables the monitor recorder 14 to be worn at all times, even during bathing or other activities that could expose the monitor recorder 14 to moisture.

In addition, a battery compartment 236 is formed on the bottom surface of the non-conductive receptacle 225, and a pair of battery leads (not shown) electrically interface the battery to another pair of the electrical pads 234. The battery contained within the battery compartment 235 can be replaceable, rechargeable or disposable.

Figure 8:
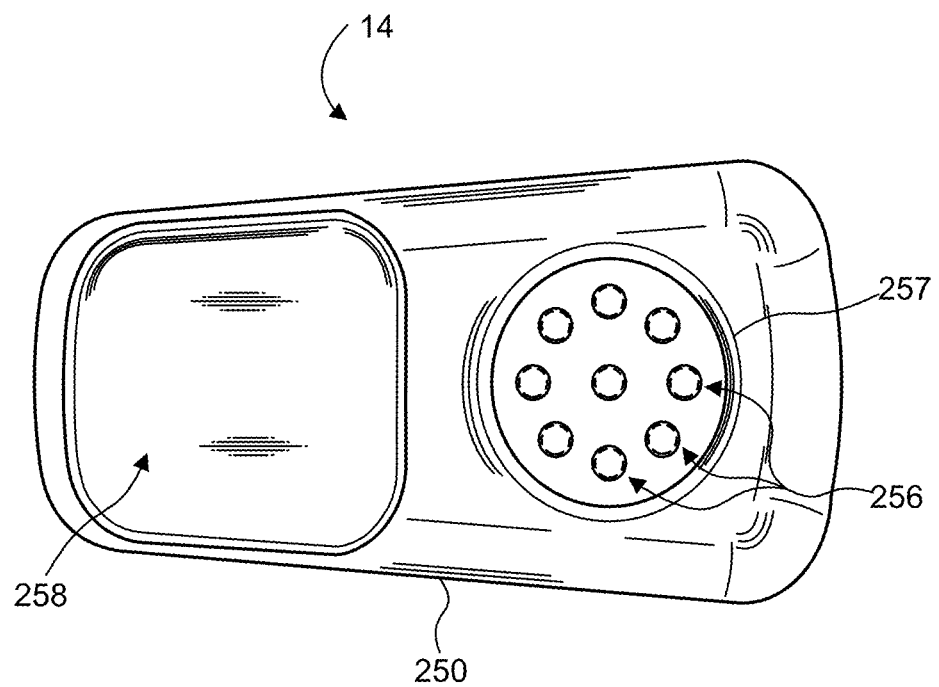
FIG. 8 is a bottom plan view of the monitor recorder of FIG. 5.

The monitor recorder 14 draws power externally from the battery provided in the non-conductive receptacle 225, thereby uniquely obviating the need for the monitor recorder 14 to carry a dedicated power source. FIG. 8 is a bottom plan view of the monitor recorder 14 of FIG. 5. A cavity 258 is formed on the bottom surface of the sealed housing 250 to accommodate the upward projection of the battery compartment 236 from the bottom surface of the non-conductive receptacle 225, when the monitor recorder 14 is secured in place on the non-conductive receptacle 225. A set of electrical contacts 256 protrude from the bottom surface of the sealed housing 250 and are arranged in alignment with the electrical pads 234 provided on the bottom surface of the non-conductive receptacle 225 to establish electrical connections between the electrode patch 15 and the monitor recorder 14. In addition, a seal coupling 257 circumferentially surrounds the set of electrical contacts 256 and securely mates with the moisture-resistant seal 235 formed on the bottom surface of the non-conductive receptacle 225.

The placement of the flexible backing 220 on the sternal midline 16 (or immediately to either side of the sternum 13) also helps to minimize the side-to-side movement of the wearable monitor 12 in the left- and right-handed directions during wear. To counter the dislodgment of the flexible backing 220 due to compressional and torsional forces, a layer of non-irritating adhesive, such as hydrocolloid, is provided at least partially on the underside, or contact, surface of the flexible backing 20, but only on the distal end 230 and the proximal end 231. As a result, the underside, or contact surface of the longitudinal midsection 223 does not have an adhesive layer and remains free to move relative to the skin. Thus, the longitudinal midsection 223 forms a crimp relief that respectively facilitates compression and twisting of the flexible backing 220 in response to compressional and torsional forces. Other forms of flexible backing crimp reliefs are possible.

Figure 9:
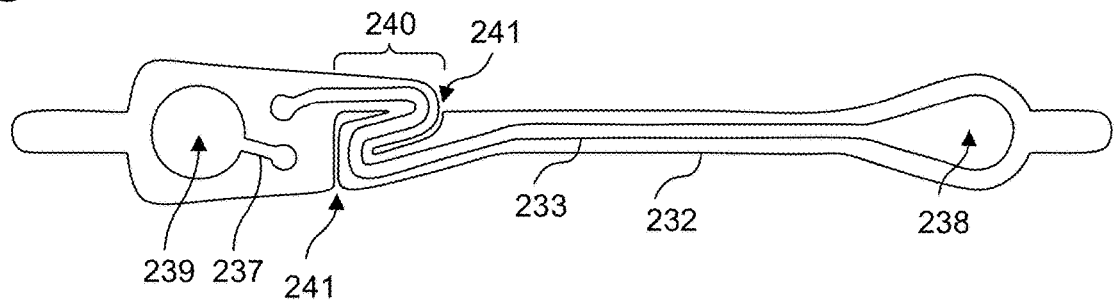
FIG. 9 is a top view showing the flexible circuit of the extended wear electrode patch of FIG. 5 when mounted above the flexible backing.

Unlike the flexible backing 20, the flexible circuit 232 is only able to bend and cannot stretch in a planar direction. The flexible circuit 232 can be provided either above or below the flexible backing 20. FIG. 9 is a top view showing the flexible circuit 232 of the extended wear electrode patch 15 of FIG. 5 when mounted above the flexible backing 20. A distal ECG electrode 238 and proximal ECG electrode 239 are respectively coupled to the distal and proximal ends of the flexible circuit 232. A strain relief 240 is defined in the flexible circuit 232 at a location that is partially underneath the battery compartment 236 when the flexible circuit 232 is affixed to the flexible backing 20. The strain relief 240 is laterally extendable to counter dislodgment of the ECG electrodes 238, 239 due to tensile and torsional forces. A pair of strain relief cutouts 241 partially extend transversely from each opposite side of the flexible circuit 232 and continue longitudinally towards each other to define in 'S'-shaped pattern, when viewed from above. The strain relief respectively facilitates longitudinal extension and twisting of the flexible circuit 232 in response to tensile and torsional forces. Other forms of circuit board strain relief are possible. Other forms of the patch 15 are also possible. For example, in a further embodiment, the distal and proximal circuit traces are replaced with interlaced or sewn-in flexible wires, as further described in in commonly-assigned U.S. Pat. No. 9,717,432, issued Aug. 1, 2017, the disclosure of which is incorporated by reference.

Figure 10:
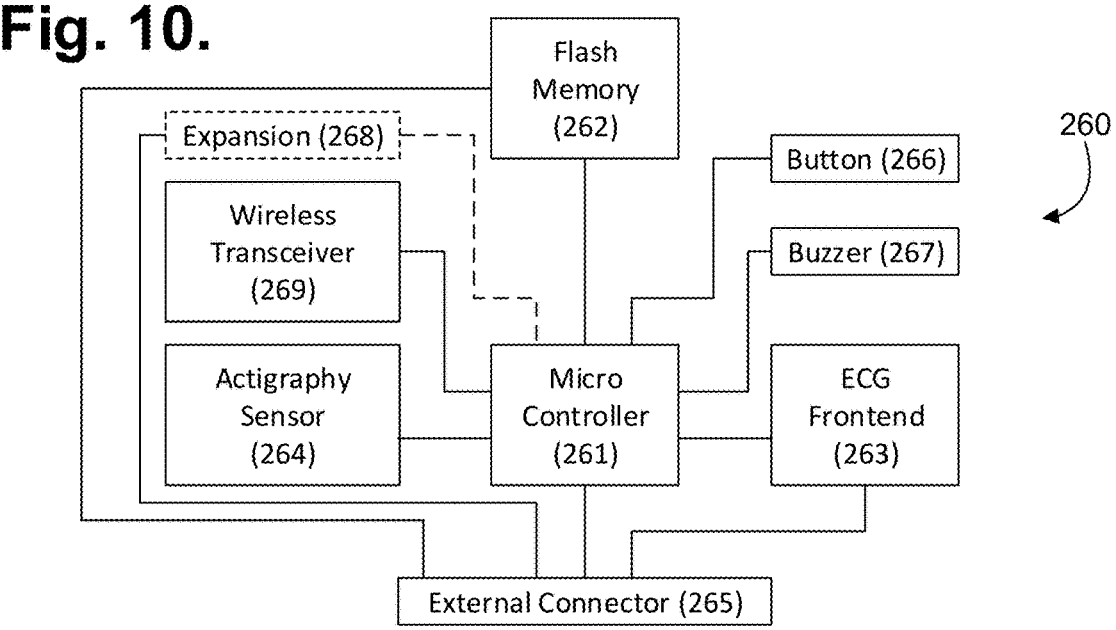
FIG. 10 is a functional block diagram showing the component architecture of the circuitry of the monitor recorder of FIG. 5.

ECG monitoring and other functions performed by the monitor recorder 14 are provided through a micro controlled architecture. FIG. 10 is a functional block diagram showing the component architecture of the circuitry 260 of the monitor recorder 14 of FIG. 5. The circuitry 260 is externally powered through a battery provided in the non-conductive receptacle 225 (shown in FIG. 6). Both power and raw ECG signals, which originate in the pair of ECG electrodes 238, 239 (shown in FIG. 9) on the distal and proximal ends of the electrode patch 15, are received through an external connector 265 that mates with a corresponding physical connector on the electrode patch 15. The external connector 265 includes the set of electrical contacts 256 that protrude from the bottom surface of the sealed housing 250 and which physically and electrically interface with the set of pads 234 provided on the bottom surface of the non-conductive receptacle 225. The external connector includes electrical contacts 256 for data download, microcontroller communications, power, analog inputs, and a peripheral expansion port. The arrangement of the pins on the electrical connector 265 of the monitor recorder 14 and the device into which the monitor recorder 14 is attached, whether an electrode patch 15 or download station (not shown), follow the same electrical pin assignment convention to facilitate interoperability. The external connector 265 also serves as a physical interface to a download station that permits the retrieval of stored ECG monitoring data, communication with the monitor recorder 14, and performance of other functions.

Operation of the circuitry 260 of the monitor recorder 14 is managed by a microcontroller 261. The microcontroller 261 includes a program memory unit containing internal flash memory that is readable and writeable. The internal flash memory can also be programmed externally. The microcontroller 261 draws power externally from the battery provided on the electrode patch 15 via a pair of the electrical contacts 256. The microcontroller 261 connects to the ECG front end circuit 263 that measures raw cutaneous electrical signals and generates an analog ECG signal representative of the electrical activity of the patient's heart over time.

Figure 11:
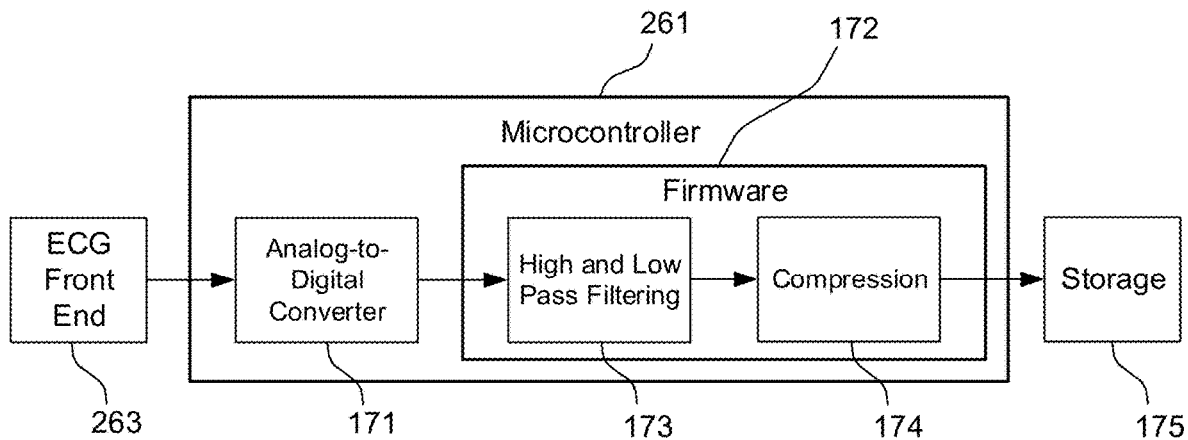
FIG. 11 is a functional block diagram showing the signal processing functionality of the microcontroller in accordance with one embodiment.

The microcontroller 261 operates under modular micro program control as specified in firmware, and the program control includes processing of the analog ECG signal output by the ECG front end circuit 263. FIG. 11 is a functional block diagram showing the signal processing functionality 170 of the microcontroller 261 in accordance with one embodiment. The microcontroller 261 operates under modular micro program control as specified in firmware 172. The firmware modules 172 include high and low pass filtering 173, and compression 174. Other modules are possible. The microcontroller 261 has a built-in ADC, although ADC functionality could also be provided in the firmware 172.

The ECG front end circuit 263 first outputs an analog ECG signal, which the ADC 171 acquires, samples and converts into an uncompressed digital representation. The microcontroller 261 includes one or more firmware modules 173 that perform filtering. In one embodiment, a high pass smoothing filter is used for the filtering; other filters and combinations of high pass and low pass filters are possible in a further embodiment. Following filtering, the digital representation of the cardiac activation wave front amplitudes are compressed by a compression module 174 before being written out to storage 175.

The circuitry 260 of the monitor recorder 14 also includes a flash memory 262, which the microcontroller 261 uses for storing ECG monitoring data and other physiology and information. The data is stored in the memory 262 together with the identifier 201 associated with the patch 15 and the password 202, which are obtained from the patch 15 as further described below. The flash memory 262 also draws power externally from the battery provided on the electrode patch 15 via a pair of the electrical contacts 256. Data is stored in a serial flash memory circuit, which supports read, erase and program operations over a communications bus. The flash memory 262 enables the microcontroller 261 to store digitized ECG data. The communications bus further enables the flash memory 262 to be directly accessed externally over the external connector 265 when the monitor recorder 14 is interfaced to a download station.

The circuitry 260 of the monitor recorder 14 further includes an actigraphy sensor 264 implemented as a 3-axis accelerometer. The accelerometer may be configured to generate interrupt signals to the microcontroller 261 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses, such as described in commonly-assigned U.S. Pat. No. 9,737,224, issued Aug. 22, 2017, the disclosure of which is incorporated by reference.

The circuitry 260 of the monitor recorder 14 includes a wireless transceiver 269 that can provides wireless interfacing capabilities. The wireless transceiver 269 also draws power externally from the battery provided on the electrode patch 15 via a pair of the electrical contacts 256. The wireless transceiver 269 can be implemented using one or more forms of wireless communications, including the IEEE 280 2.11 computer communications standard, that is Wi-Fi; the 4G mobile phone mobile standard; the Bluetooth® data exchange standard; or other wireless communications or data exchange standards and protocols. For example, the wireless transceiver 69 can be implemented using the Bluetooth® 4.0 standard, allowing to conserve power, or Bluetooth® 4.2 standards, allowing the transceiver 69 to have at least some capabilities of a cellular phone, as further described in the commonly-assigned U.S. Pat. No. 10,667,711, issued Jun. 2, 2020, the disclosure of which is incorporated by reference.

The microcontroller 261 includes an expansion port that also utilizes the communications bus. External devices, separately drawing power externally from the battery provided on the electrode patch 15 or other source, can interface to the microcontroller 261 over the expansion port in half duplex mode. For instance, an external physiology sensor can be provided as part of the circuitry 260 of the monitor recorder 14, or can be provided on the electrode patch 15 with communication with the microcontroller 261 provided over one of the electrical contacts 256. The physiology sensor can include an $SpO_2$ sensor, blood pressure sensor, temperature sensor, respiratory rate sensor, glucose sensor, airflow sensor, volumetric pressure sensing, or other types of sensor or telemetric input sources. For instance, the integration of an airflow sensor is described in commonly-assigned U.S. Pat. No. 9,364,155, issued Jun. 14, 2016, the disclosure which is incorporated by reference.

Finally, the circuitry 260 of the monitor recorder 14 includes patient-interfaceable components, including a tactile feedback button 266, which a patient can press to mark events or to perform other functions, and a buzzer 267, such as a speaker, magnetic resonator or piezoelectric buzzer. The buzzer 267 can be used by the microcontroller 261 to output feedback to a patient such as to confirm power up and initiation of ECG monitoring. Still other components as part of the circuitry 260 of the monitor recorder 14 are possible.

Figure 12:
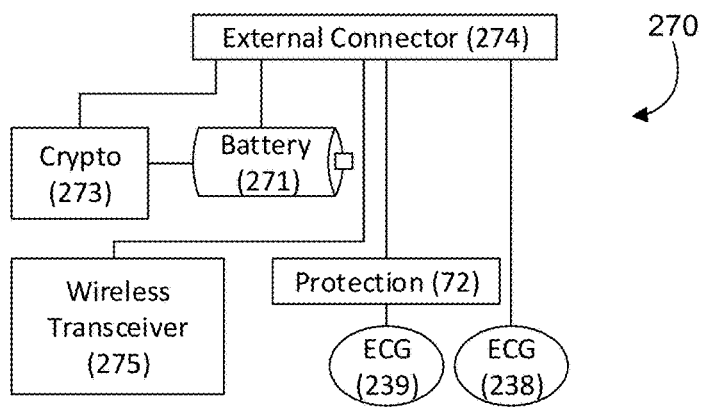
FIG. 12 is a functional block diagram showing the circuitry of the extended wear electrode patch of FIG. 5.

While the monitor recorder 14 operates under micro control, most of the electrical components of the electrode patch 15 operate passively. FIG. 12 is a functional block diagram showing the circuitry 270 of the extended wear electrode patch 15 of FIG. 4. The circuitry 270 of the electrode patch 15 is electrically coupled with the circuitry 260 of the monitor recorder 14 through an external connector 274. The external connector 274 is terminated through the set of pads 234 provided on the bottom of the non-conductive receptacle 225, which electrically mate to corresponding electrical contacts 256 protruding from the bottom surface of the sealed housing 250 to electrically interface the monitor recorder 14 to the electrode patch 15.

The circuitry 270 of the electrode patch 15 performs three primary functions. First, a battery 271 is provided in a battery compartment formed on the bottom surface of the non-conductive receptacle 225. The battery 271 is electrically interfaced to the circuitry 260 of the monitor recorder 14 as a source of external power. The unique provisioning of the battery 271 on the electrode patch 15 provides several advantages. First, the locating of the battery 271 physically on the electrode patch 15 lowers the center of gravity of the overall wearable monitor 12 and thereby helps to minimize shear forces and the effects of movements of the patient and clothing. Moreover, the housing 250 of the monitor recorder 14 is sealed against moisture and providing power externally avoids having to either periodically open the housing 250 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 261. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 260.

Second, the pair of ECG electrodes 238, 239 respectively provided on the distal and proximal ends of the flexible circuit 232 are electrically coupled to the set of pads 234 provided on the bottom of the non-conductive receptacle 225 by way of their respective circuit traces 233, 237. The signal ECG electrode 239 includes a protection circuit 272, which is an inline resistor that protects the patient from excessive leakage current.

Last, the circuitry 270 of the electrode patch 15 includes a cryptographic circuit 273 that stores an encoded password 202 for accessing data collecting using this patch 15. The password 202 is encrypted using the secret key 203 to prevent an unauthorized party from obtaining the password 202 once the patch 15 is discarded by the patient. The password 202 is encrypted using a secret key of which the micro-controller 261 has a copy. Thus, only the micro-controller 261 can interface with the cryptographic circuit 273 to obtain the password 202 and decode the password 202 using the secret key, which can be stored in the memory 262. The cryptographic circuit can further store the identifier 201 associated with that patch and the identifier 201 can also be retrieved by the micro-controller 261. In one embodiment, the identifier 201 can be encrypted; in a further embodiment, the identifier 201 can be unencrypted.

In a further embodiment, the cryptographic circuit 73 could be used to authenticate an electrode patch 15 for use with a monitor recorder 14. The cryptographic circuit 273 includes a device capable of secure authentication and validation. The cryptographic device 273 ensures that only genuine, non-expired, safe, and authenticated electrode patches 15 are permitted to provide monitoring data to a monitor recorder 14, such as described in commonly-assigned U.S. Pat. No. 9,655,538, issued May 23, 2017, the disclosure which is incorporated by reference.

Figure 13:
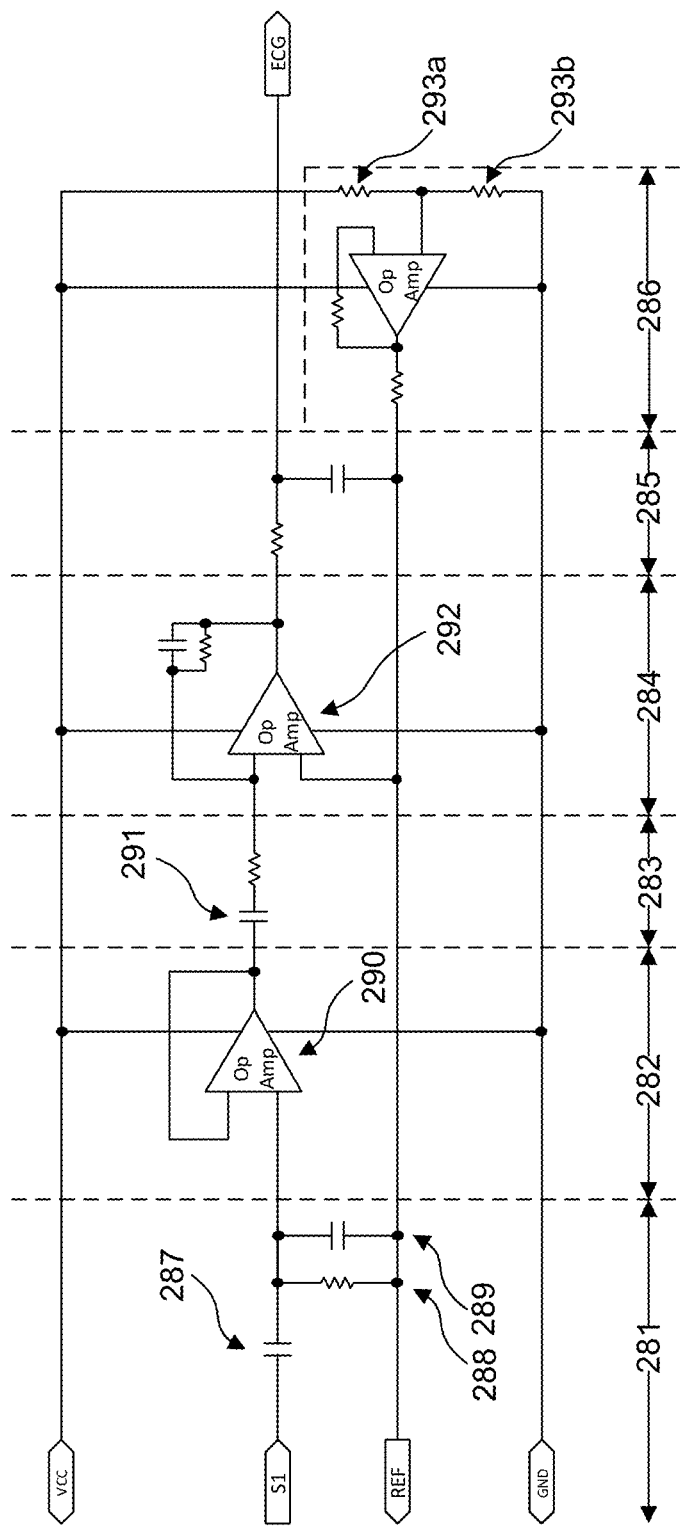
FIG. 13 is a schematic diagram showing the ECG front end circuit of the circuitry of the monitor recorder of FIG. 10 in accordance with one embodiment.

The ECG front end circuit 263 measures raw cutaneous electrical signals using a driven reference that effectively reduces common mode noise, power supply noise and system noise, which is critical to preserving the characteristics of low amplitude cardiac action potentials, especially those signals from the atria. FIG. 13 is a schematic diagram 280 showing the ECG front end circuit 263 of the circuitry 260 of the monitor recorder 14 of FIG. 9 in accordance with one embodiment. The ECG front end circuit 263 senses body surface potentials through a signal lead ("S1") and reference lead ("REF") that are respectively connected to the ECG electrodes of the electrode patch 15. Power is provided to the ECG front end circuit 263 through a pair of DC power leads ("VCC" and "GND"). An analog ECG signal ("ECG") representative of the electrical activity of the patient's heart over time is output, which the micro controller 11 converts to digital representation and filters, as further described infra.

The ECG front end circuit 263 is organized into five stages, a passive input filter stage 281, a unity gain voltage follower stage 282, a passive high pass filtering stage 283, a voltage amplification and active filtering stage 284, and an anti-aliasing passive filter stage 285, plus a reference generator. Each of these stages and the reference generator will now be described.

The passive input filter stage 281 includes the parasitic impedance of the ECG electrodes 238, 239 (shown in FIG. 12), the protection resistor that is included as part of the protection circuit 272 of the ECG electrode 239 (shown in FIG. 12), an AC coupling capacitor 287, a termination resistor 288, and filter capacitor 289. This stage passively shifts the frequency response poles downward there is a high electrode impedance from the patient on the signal lead S1 and reference lead REF, which reduces high frequency noise.

The unity gain voltage follower stage 282 provides a unity voltage gain that allows current amplification by an Operational Amplifier ("Op Amp") 290. In this stage, the voltage stays the same as the input, but more current is available to feed additional stages. This configuration allows a very high input impedance, so as not to disrupt the body surface potentials or the filtering effect of the previous stage.

The passive high pass filtering stage 283 is a high pass filter that removes baseline wander and any offset generated from the previous stage. Adding an AC coupling capacitor 291 after the Op Amp 290 allows the use of lower cost components, while increasing signal fidelity.

The voltage amplification and active filtering stage 284 amplifies the voltage of the input signal through Op Amp 291, while applying a low pass filter. The DC bias of the input signal is automatically centered in the highest performance input region of the Op Amp 291 because of the AC coupling capacitor 291.

The anti-aliasing passive filter stage 285 provides an anti-aliasing low pass filter. When the microcontroller 261 acquires a sample of the analog input signal, a disruption in the signal occurs as a sample and hold capacitor that is internal to the microcontroller 261 is charged to supply signal for acquisition.

The reference generator in subcircuit 286 drives a driven reference containing power supply noise and system noise to the reference lead REF. A coupling capacitor 287 is included on the signal lead S1 and a pair of resistors 293a, 293b inject system noise into the reference lead REF. The reference generator is connected directly to the patient, thereby avoiding the thermal noise of the protection resistor that is included as part of the protection circuit 272.

In contrast, conventional ECG lead configurations try to balance signal and reference lead connections. The conventional approach suffers from the introduction of differential thermal noise, lower input common mode rejection, increased power supply noise, increased system noise, and differential voltages between the patient reference and the reference used on the device that can obscure, at times, extremely, low amplitude body surface potentials.

Here, the parasitic impedance of the ECG electrodes 238, 239, the protection resistor that is included as part of the protection circuit 272 and the coupling capacitor 287 allow the reference lead REF to be connected directly to the skin's surface without any further components. As a result, the differential thermal noise problem caused by pairing protection resistors to signal and reference leads, as used in conventional approaches, is avoided.

In a further embodiment, the circuitry 270 of the electrode patch 15 includes a wireless transceiver 275, in lieu the including of the wireless transceiver 269 in the circuitry 260 of the monitor recorder 14, which interfaces with the microcontroller 261 over the microcontroller's expansion port via the external connector 274. Similarly to the wireless transceiver 269, the wireless transceiver 275 can be implemented using a standard that allows to conserve battery power, such as the Bluetooth® 4.0 standard, though other standards are possible. Further, similarly to the wireless transceiver 269, the wireless transceiver 275 can be implemented using a standard that allows the transceiver 275 to act have cellular phone capabilities, such as the Bluetooth® 4.2 standard.

Figure 14:
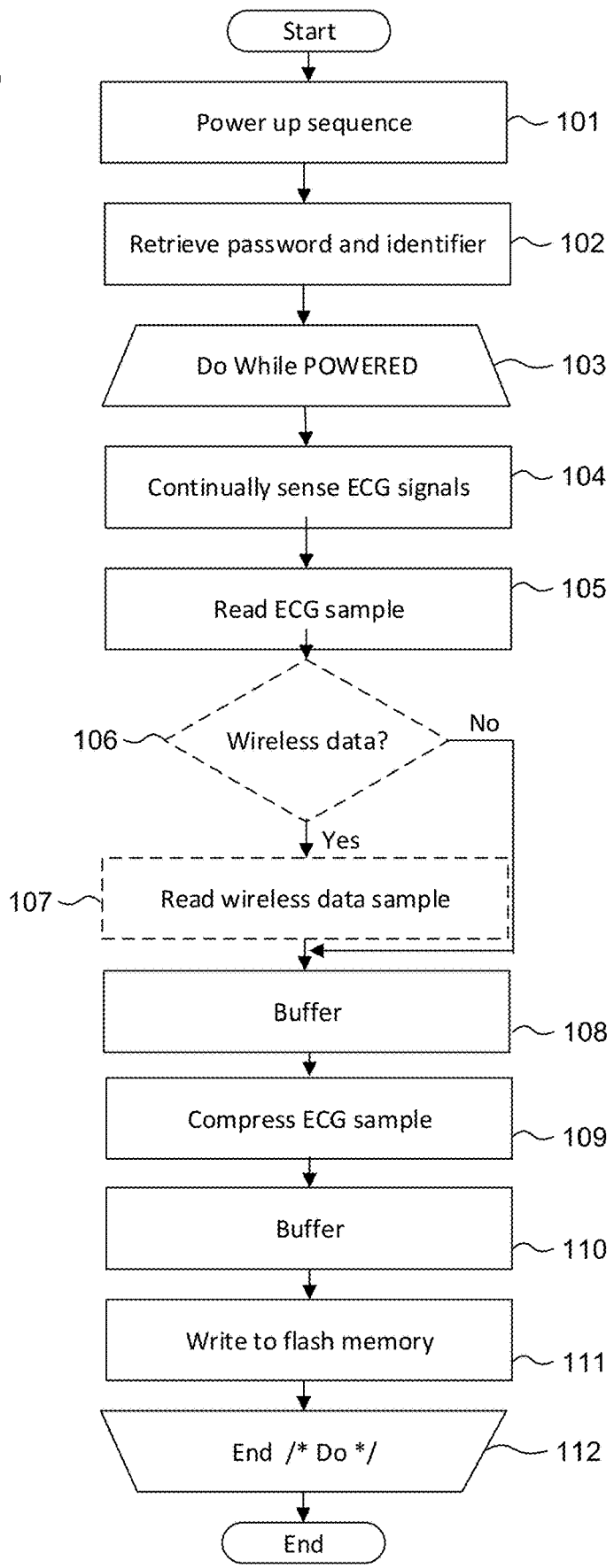
FIG. 14 is a flow diagram showing a monitor recorder-implemented method for monitoring ECG data for use in the monitor recorder of FIG. 5.

The monitor recorder 14 continuously monitors the patient's heart rate and physiology. FIG. 14 is a flow diagram showing a monitor recorder-implemented method 100 for monitoring ECG data for use in the monitor recorder 14 of FIG. 4. Initially, upon being connected to the set of pads 234 provided with the non-conductive receptacle 225 when the monitor recorder 14 is snapped into place, the microcontroller 261 executes a power up sequence (step 101). During the power up sequence, the voltage of the battery 271 is checked, the state of the flash memory 262 is confirmed, both in terms of operability check and available capacity, and microcontroller operation is diagnostically confirmed. In a further embodiment, an authentication procedure between the microcontroller 261 and the electrode patch 15 are also performed.

The micro-controller 61 retrieves and, as necessary, decodes the password 202 and the identifier 201 associated with the electrode patch 15 (step 102). Subsequent physiological data obtained using the patch 15 is stored in the memory 262 with the password 202 and the identifier in plaintext, unencrypted, form.

Figure 15:
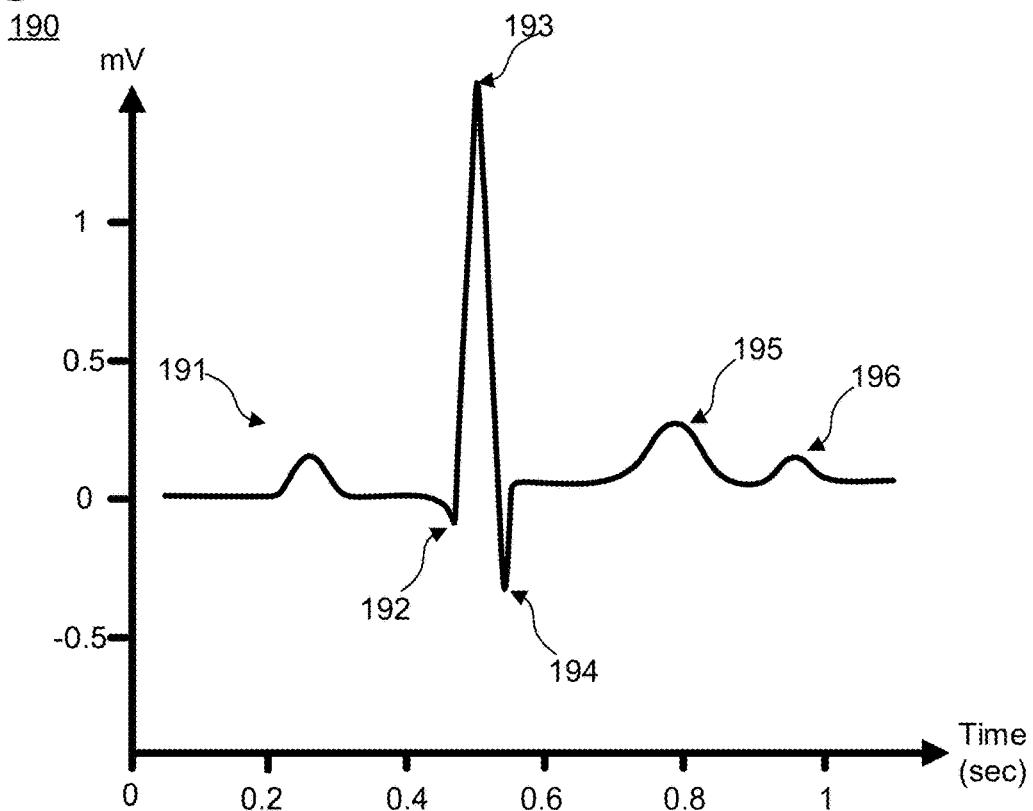
FIG. 15 is a graph showing, by way of example, a typical ECG waveform.

Following satisfactory completion of the power up sequence and the decoding, an iterative processing loop (steps 103-112) is continually executed by the microcontroller 261. During each iteration (step 103) of the processing loop, the ECG front end 263 (shown in FIGS. 9 and 15) continually senses the cutaneous ECG electrical signals (step 104) via the ECG electrodes 238, 239 and is optimized to maintain the integrity of the P-wave. A sample of the ECG signal is read (step 105) by the microcontroller 261 by sampling the analog ECG signal output front end 263. FIG. 15 is a graph showing, by way of example, a typical ECG waveform 190. The x-axis represents time in approximate units of tenths of a second. The y-axis represents cutaneous electrical signal strength in approximate units of millivolts. The P-wave 191 has a smooth, normally upward, that is, positive, waveform that indicates atrial depolarization. The QRS complex usually begins with the downward deflection of a Q wave 192, followed by a larger upward deflection of an R-wave 193, and terminated with a downward waveform of the S wave 194, collectively representative of ventricular depolarization. The T wave 195 is normally a modest upward waveform, representative of ventricular depolarization, while the U wave 196, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Returning to FIG. 14, in a further embodiment, the monitor recorder 14 also continuously receives data from wearable physiology monitors or activity sensor, such as described in commonly-assigned U.S. Patent Application Publication No. 2015/0088007, published Mar. 26, 2015, the disclosure of which is incorporated by reference. Optionally, If wireless data is available (step 106), a sample of the wireless is read (step 107) by the microcontroller 61. If wireless data is not available (step 106), the method 100 moves to step 108.

Each sampled ECG signal, in quantized and digitized form, is temporarily staged in buffer (step 108), pending compression preparatory to storage in the flash memory 262 (step 109). If wireless data sample was read in step 106, the wireless data sample, in quantized and digitized form, is temporarily staged in the buffer (step 108), pending compression preparatory to storage in the flash memory 62 (step 109). Following compression, the compressed ECG digitized sample, and if present, the wireless data sample, is again buffered (step 110), then written to the flash memory 262 (step 111) using the communications bus. Processing continues (step 112), so long as the monitoring recorder 14 remains connected to the electrode patch 15 (and storage space remains available in the flash memory 262), after which the processing loop is exited and execution terminates. Still other operations and steps are possible. In a further embodiment, the reading and storage of the wireless data takes place, in a conceptually-separate execution thread, such as described in commonly-assigned U.S. Patent Application Publication No. 2015/0088007, published Mar. 26, 2015, to Bardy et al., the disclosure of which is incorporated by reference.

Once ECG data is collected by the monitor 12, the data can undergo various kinds of processing. In particular, the ECG data can undergo additional filtering to further remove noise. An ECG includes multiple waveforms reflecting multiple contractions of a patient's heart. ECG signals include low amplitude voltages in the presence of high offsets and noise, which requires the signals to be amplified and filtered prior to being displayed for interpretation. In an unfiltered ECG, some of the features may not be apparent, particularly if their shapes have been corrupted by noise. For example, the P-wave morphology, presence or absence, timing, and size can be indicative of a variety of cardiac conditions. An abnormally large P-wave can be indicative of atrial hypertrophy, an abnormally wide P-wave can be indicative of an intra-atrial block, and atrial flutter may cause the P-waves to adopt a "saw-tooth" or negative shape. Absent or not-easily discernible P-waves can be indicative of atrial fibrillation, while discrete P-waves that vary from beat-to-beat with at least three different morphologies, can be indicative of multifocal atrial tachycardia. A dissociation between the timing of the P-wave and the QRS complex can indicate ventricular tachycardia. Other associations between the P-wave and cardiac conditions exist. Identifying presence, timing and morphology or the P-wave is critical to arrhythmia diagnosis.

Figure 16:
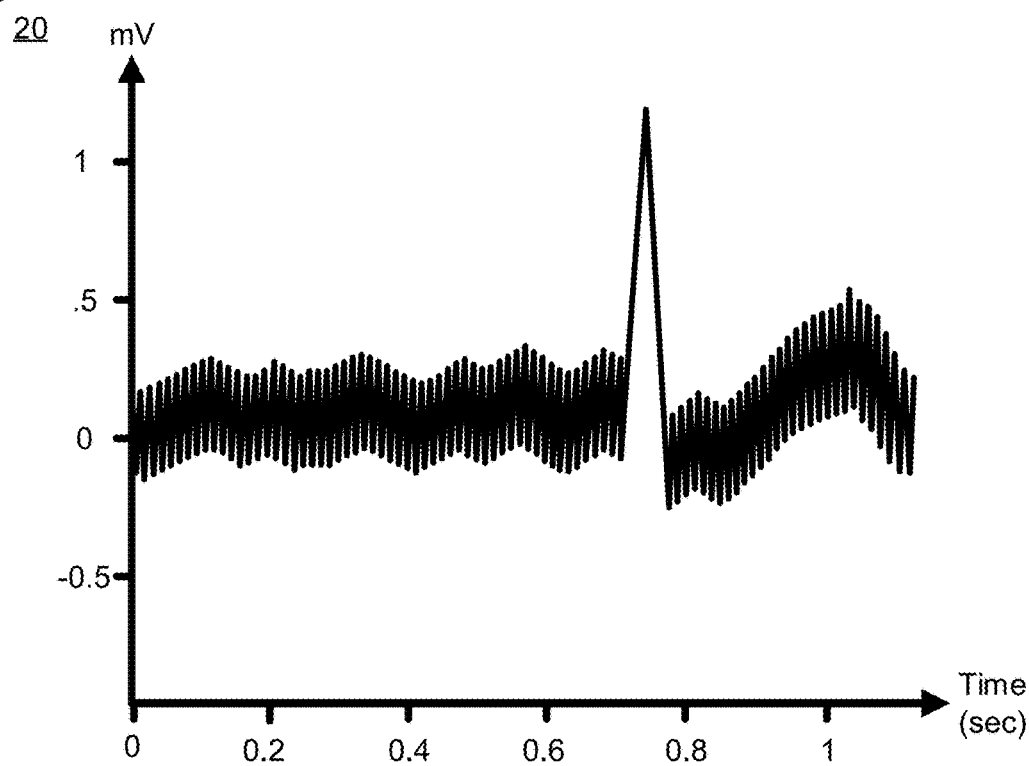
FIG. 16 is a graph showing, by way of example, an ECG waveform of a patient with atrial flutter for a single cardiac cycle, where the ECG waveform has been corrupted by power line noise.

Noise in an ECG or inadequate signal clarity is a major problematic for cardiologists when caring for patients with possible cardiac arrhythmias. FIG. 16 is a graph showing, by way of example, an ECG waveform 20 of a patient with atrial flutter for a single cardiac cycle, where the ECG waveform 20 has been corrupted by power line noise. In the United States, power line noise has a frequency of 60 Hz with a high amplitude. The wall outlets in an examination room invariably surround a patient and create an electrical field that causes power line noise to be coupled into the ECG. Here the patient's ECG lacks a clearly defined P-wave, with the signal noise obscuring the "saw-tooth" P-wave shape seen in the underlying atrial flutter. As a result, the diagnosis is missed.

Classical ways to reduce power line noise are to make physical changes to the circuit design of ECG equipment. For instance, power line noise can be reduced by isolating front-end ground electronics from the digital components of the machine, and using shielded cables to acquire ECG signals driven with a common voltage to reduce noise from being coupled from proximal power lines. However, some degree of power line noise will always be present due to the power draw of the ECG machine itself. Power line noise is more predictable and more readily lends itself to classical noise-reduction techniques, as described above.

Other types of noise, such as those associated with muscle activity, often the main source of ECG noise, including baseline wander, is best diminished with a more patient-specific and dynamic method of noise reduction involving the appropriate application of digital noise filters.

Digital filters are inherently flexible. Changing the characteristics of a digital filter merely involves changing the program code or filter coefficients. They also do not require physical reconstruction of the ECG system, and thus tend to be low cost and highly compatible with existing ECG equipment. Noise present in an ECG of one patient can be different from noise present in an ECG of another patient, and the flexibility provided by the digital filters helps to clarify each individual ECG and provide for patient-specific ECG signal processing. In addition, digital filters are immune to the effects of wear and degradation that all hardware experiences.

Figure 17:
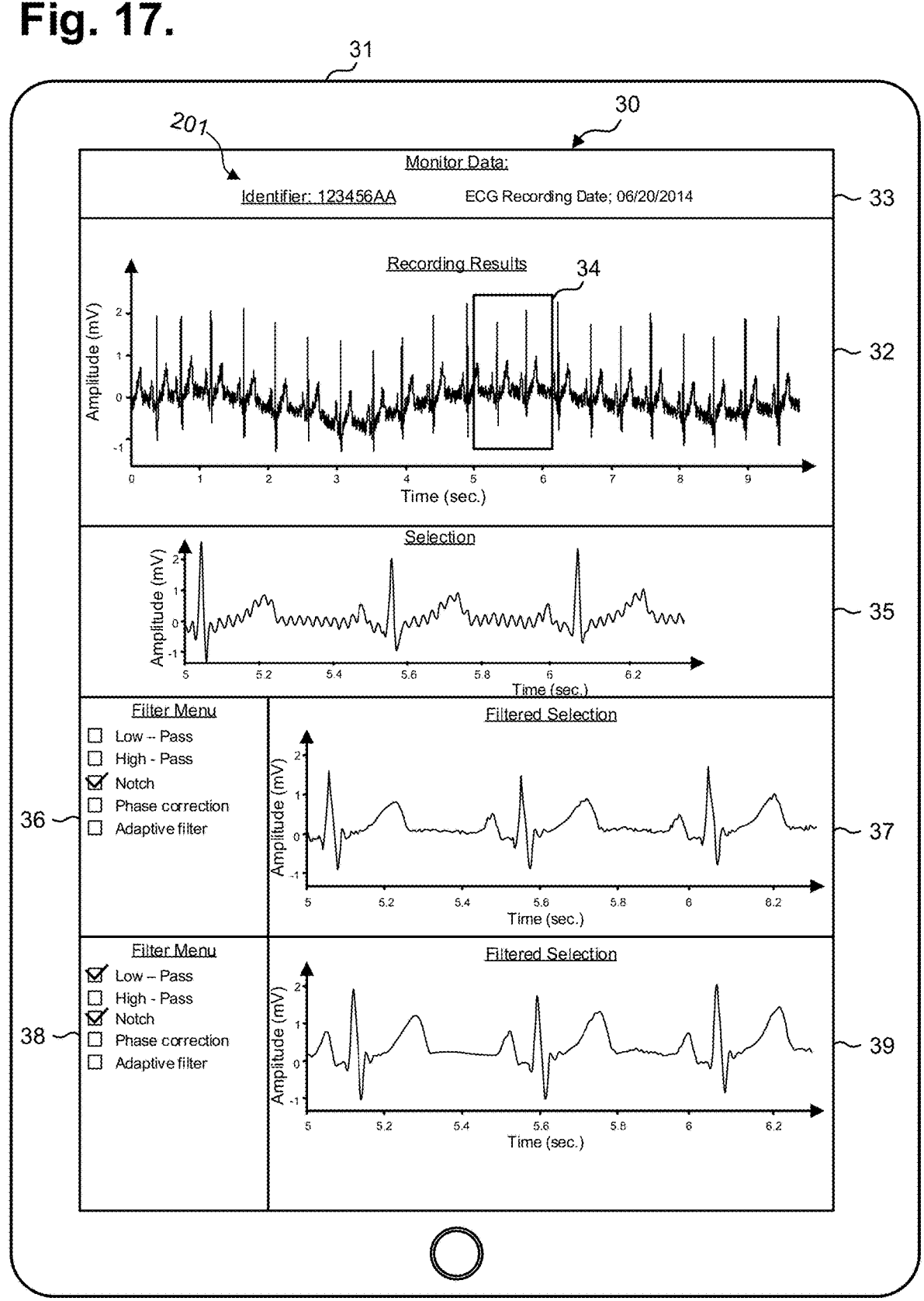
FIG. 17 is a diagram showing a screen shot generated by an application for interactive processing of ECG data in accordance with one embodiment.

ECG noise can be effectively reduced by allowing a user to pick particular portions of an ECG for application of a filter and allowing the user to compare results of applications of different filters to the selected portions. This is critical when seeking to record the more difficult-to-see P-wave compared to the high voltage high frequency content of the QRS wave. FIG. 17 is a diagram showing a screen shot generated by an application 30 for interactive processing of ECG data in accordance with one embodiment. The application 30 can be a downloadable application executed on a user device 31. While the user device 31 is shown as a tablet computer with reference to FIG. 4, other kinds of user devices 31, such as mobile phones, desktop computer, laptop computers, portable media players are possible; still other types of user devices 31 are possible. The user device 31 can include components conventionally found in general purpose programmable computing devices, such as a central processing unit, memory, input/output ports, network interfaces, and non-volatile storage, although other components are possible. The central processing unit can implement computer-executable code, including digital ECG filters, which can be implemented as modules. The modules can be implemented as a computer program or procedure written as source code in a conventional programming language and presented for execution by the central processing unit as object or byte code. Alternatively, the modules could also be implemented in hardware, either as integrated circuitry or burned into read-only memory components, and the user device starts acting a specialized computer. For instance, when the modules are implemented as hardware, that particular hardware is specialized to perform the ECG trace analysis described below and other computers cannot be used. Additionally, when the modules are burned into read-only memory components, the user device 31 storing the read-only memory becomes specialized to perform the ECG processing described below that other computers cannot. The various implementations of the source code and object and byte codes can be held on a computer-readable storage medium, such as a floppy disk, hard drive, digital video disk (DVD), random access memory (RAM), read-only memory (ROM) and similar storage mediums. Other types of modules and module functions are possible, as well as other physical hardware components.

The application 30 receives results of an ECG monitoring, which can include an ECG 32, including in a printed form. The ECG 32 can be received at once, such as upon completion of monitoring, or in portions, as the monitoring progresses. In addition to the ECG 32, the application 30 the identifier 201 associated with the patch 15 used for data collection.

A user may select a portion 34 of the displayed ECG 32 for application of one or more digital filters, such as by clicking on the portion or highlighting the portion with a mouse. The selected portion 34 can be zoomed and displayed in a separate area 35 of the application screen. By looking at the selection in the area 35, the user can decide what filters to apply to the selection 34.

Application of filters to an ECG can result in a loss of clinical information present in the ECG waves. Only a limited number of filters can be applied before such clinical information is lost due to the filters introducing distortions into some part of the ECG signals. For example, a high-pass filter, a filter whose purpose is to remove low-frequency noise, introduces distortions to the ST segment of ECG. The distortion arises from the combination of the frequencies of some of the noise overlapping with the spectra of useful ECG waves, with the noise generally being stochastic; thus any attempt of removing the noises after signal acquisition is typically accompanied by some degree of signal degradation. An excessive number or an incorrect set of applied filters can remove useful diagnostic features from the ECG waveform, leading to false diagnostic statements. By selecting a portion 34 of the ECG and, applying filters only to that portion, the rest of the ECG 32 is maintained intact and unfiltered.

The user may filter the selection 34 using a list of ECG digital noise filters provided by application in filter selection menus 36, 38. By selecting the filters in different menus 36, 38, the user can select different sets of filters for filtering the ECG 32. Each of the digital filters is a mathematical algorithm that is applied to digital ECG signals to output a set of filtered signals that differs from the set of the ECG signals to which that filter is initially applied. The filters can be stored in the memory of the user device 31. Such filters can include a low-pass filter, which attenuates noise with a frequency higher than a cut-off frequency; a high-pass filter, which attenuates signals with frequencies lower than the cut-off frequency; a notch filter, which passes all frequencies except those in a stop-band centered on a center frequency; a phase correction filter, which corrects a phase of an ECG wave following earlier digital processing; and an adaptive filter, which obtains the frequency of the noise present, such as based on patient input or by calculating the noise, and minimizes the identified noise. Other types of filters are possible.

The user can customize the filter selection menus 36, 38. For instance, the user can change the order in which the filters are displayed in the selection menus 36, 38, such as by dragging and dropping the filters with a mouse. Thus, if the user uses particular filters more often than other filters, the more used filters can be brought to the top of the menus 36, 38. Further, the order of the filters in the filter selection menu 36 can be different from the order in the menu 38.

Also, the user can select the displayed filters, such as by clicking on a name of one of the filters, and change one or more parameters of the selected filter. For example, if the selected filter is a high-pass filter, the user can enter a cut-off frequency used for the filter. Other parameters can also be changed. The desired parameters can be changed in a separate window of the application 32 that appears upon the filter being selected, though other ways for the user to change the parameters are possible. Still other ways to customize the filter selection menus are possible.

The user may apply different filters or combinations of filters to the selection 34, and see the results of applications of different filters side-by-side in the areas 37 and 39. For example, the user may select a notch filter to be applied to the selection 34, and see the results of the application of the filter, a filtered ECG of the selection, in the area 37. While the application of the notch filter results in a clearer shape of the selection 34, including that of the P-wave, if the user is still not satisfied with the result, the user can choose in the filter selection menu 38 to choose to apply a different set of filters, choosing the notch filter in combination with the low-pass filter to further remove the noise from the selection 34, with the results of the application of the filters being displayed in the area 39. The user can compare the application of different selected filters side-by-side and decide whether any of the applied filters or combinations of filters produce a satisfactory result or whether applications of other filters are necessary. The results of application of different filters to the selection 34 are displayed to the user immediately upon becoming available, allowing the user to explore different filter set possibilities in real-time and reducing the time necessary to find the most appropriate filter set.

If the user is satisfied with a filtered ECG of the selection in the area 37 or 39, the user can replace the selection 34 of the ECG 32 with the filtered ECG of the selection in area 37 or 39, such as by dragging the selection in the area 37, 39 to the displayed ECG 32 or pressing a button on the screen of the application 31 (not shown).

While two sets of filter selection menus 36, 38 and areas with the results of filter application 38, 39 are shown in the screen of the application, in a further embodiment, other numbers of filter menus and areas showing results of the filtering using the selected filters are possible.

As further described with reference to FIGS. 17 and 1, the application 30 can make a recommendation (not shown) of one or more filters to be applied to the selection 34. The recommendation is created by identifying a frequency of a noise recurring in the selection 34 ("recursive noise"), such as presence of 60 Hz power line noise, based on one or more of user input or mathematical estimation of the noise frequency, and recommending the frequency based on the noise. For example, if the recursive noise includes power line noise, a notch filter or a low-pass filter can be recommended to remove the noise. The recommendation can be presented in different ways, such as presenting the recommendation in a separate field on the screen of the application 30 or by highlighting the filters presented in the menus 36, 38.

In a further embodiment, in addition to providing a filtering recommendation, the application 30 can automatically apply one or more filters to an ECG prior to presenting the ECG to the user, saving the user the labor of filtering noise that can be automatically identified and removed. The application 30 can identify the presence of noise in an ECG received from an ECG monitor or from another source, automatically apply a filter or a combination of filters to digitized signals for portions of the ECG with the noise, and generate the ECG 32 that is displayed to the user based on digitized signals that have been filtered and any digitized signals that did not include the noise. For example, if the application 30 identifies baseline wander corrupting a received ECG, which can be identified using techniques such as measuring deviation of signals from the baseline in a random fashion within set frequency domains, the application 30 can automatically apply a filter or a set of filters to digitized signals for portions of the ECG with the baseline wander, and generate the ECG 32 displayed to the user based on digitized signals that have been filtered and signals that have not been corrupted by the baseline wander. The filters to be applied can be determined via testing, such by as applying different filters, such as various high-pass filters, or combinations of filters to the digitized signals and identifying the filters or combinations of filters that result in the greatest reduction of the baseline wander. In a further embodiment, a preset filter or combination of filters can be used to automatically reduce or remove the baseline wander. In a still further embodiment, the application 30 can also test effect of changing parameters of the filters on the removal of the noise, and choose the most appropriate parameters for the filters used. Other kinds of automated application of filters are possible.

Allowing a user to choose and selectively apply filters to selected portions of an ECG facilitates obtaining an ECG that includes discernible diagnostic information and can be used for patient diagnosis. FIG. 8 is a flow diagram showing a method 60 for interactive processing of ECG data in accordance with one embodiment. Initially, an ECG 32 that is a result of electrocardiographic monitoring of a patient is obtained by the application 30 executed on the user device 31 (step 61). The ECG 32 can be obtained from an ECG monitor or from other sources, as described above, and can be obtained upon a completion of the monitoring, or continuously received in real-time as monitoring progresses. In a still further embodiment, both the ECG 32 and the digitized ECG signals corresponding to the ECG 32 can be obtained.

Optionally, if the application 30 identifies presence of noise, such as baseline wander, in the ECG received from a monitor or another source, the application 30 can automatically apply one or more filters to digitized signals corresponding to portions of the obtained ECG that has the noise, with the ECG 32 that is subsequently displayed to the user being generated based on the filtered digitized signals and signals for portions of the ECG that did not include the baseline wander, as further described above with reference to FIG. 6 (step 62).

The ECG 32, after having been optionally automatically filtered, is displayed on a display screen of the user device 31 (step 63). If the ECG 32 is received over a period of time, such as when the ECG is a result of an ongoing electrocardiographic monitoring, portions of the ECG can be updated in real-time as they are being received, with the displayed ECG being updated as more results of the monitoring become available. If the ECG 32 is a result of an already completed monitoring, all portions of the ECG can be displayed at the same time.

A user selection 34 of a portion of the ECG is received, such as via the user touching the portion on the touch-screen display of the user device 31, entering the selection from a keyboard, or using a mouse (step 64). Digitized ECG signals corresponding to the selected portion 34 of the ECG are obtained by the application 30 (step 65). If the digitized signals for the ECG 32 were received with the ECG 32, the signals corresponding to the selection 34 can be identified among the received signals. If no digitized ECG signals have been received, the application 30 can reconstruct the digitized signals from the selection 34. Other ways to obtain the digitized signals are possible.

Optionally, the selection is zoomed and the zoomed selection 35 is displayed to the user by the application (step 66). A list, such as in the selection menus 36, 38, of a plurality of digital ECG filters for filtering the selection is displayed to the user, with the user being able to select one or more sets of the filters for filtering the selection (step 67). Optionally, a filter recommended for processing the selection 34 is determined and displayed to the user, as further described with reference to FIG. 9 (step 68). A user selection of one or more sets of the filters is received by the application 30, with each of the filter sets including at least one of the filters displayed (step 69). The application 30 applies each of the sets of the selected filters to the digitized ECG signals for the selection (step 70), generates filtered ECG for the selection based on the digital signals filtered by each of the sets, and displays the filtered ECG for the selection on portions 37, 39 of the display screen of the user device 31 (step 71). The filtered ECGs can be displayed visually proximate to each other, allowing comparison of results of filtering side-by-side, and thus enabling the user to decide which of the results is more useful, whether one of the results satisfies the user's needs, or whether a still different set of filters needs to be applied. Optionally, upon receiving a user selection of one of the filtered ECGs for the selection, the application 30 can replace the selected portion 34 of the ECG 32 with the selected filtered ECG (step 72), ending the method 60.

Figure 18:
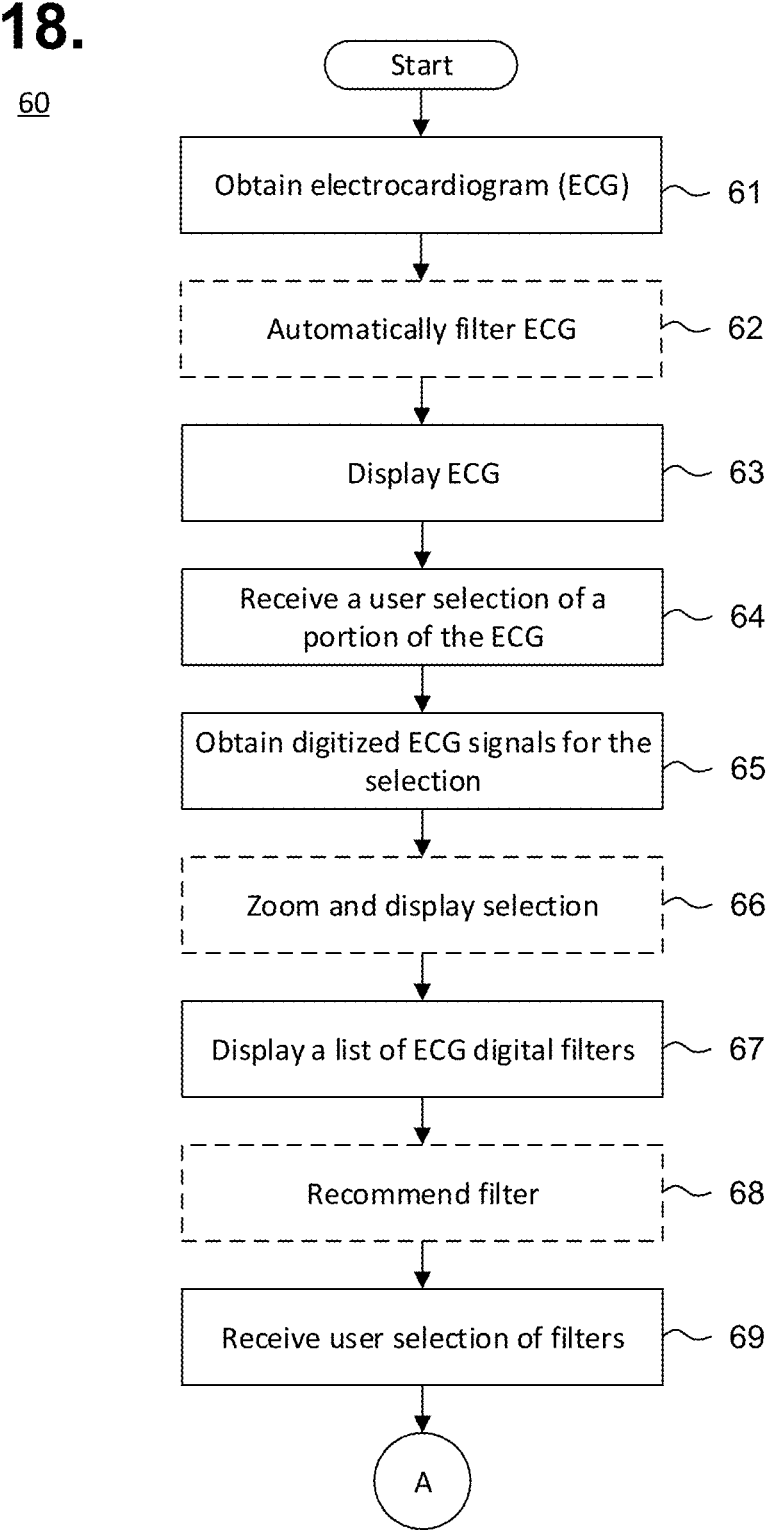
FIG. 18 is a flow diagram showing a method for interactive processing of ECG data in accordance with one embodiment.
Figure 19:
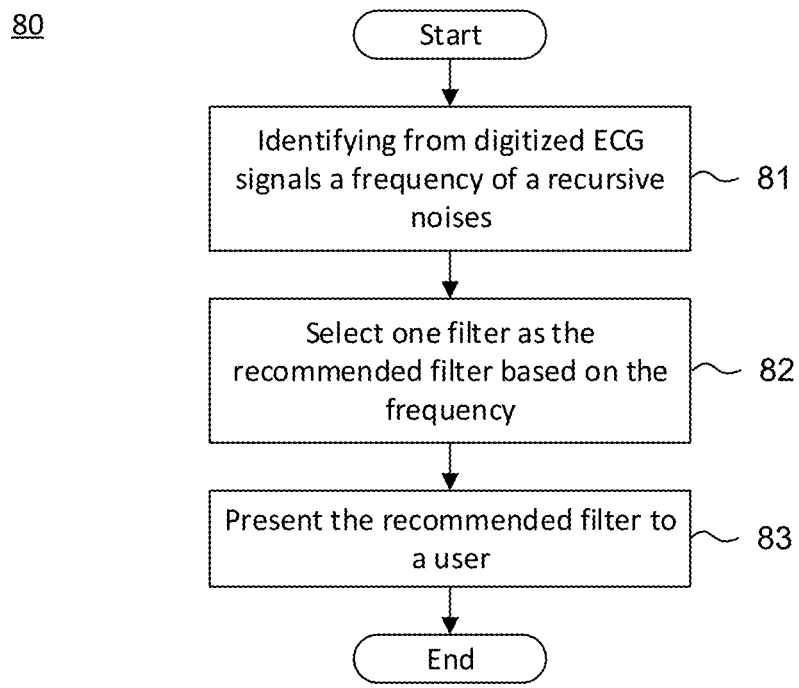
FIG. 19 is a flow diagram showing a routine for recommending an ECG filter for use in the method of FIG. 18 in accordance with one embodiment.

Recommending an ECG filter to the user can save the user time and simplify ECG interpretation for the user. FIG. 19 is a flow diagram showing a routine 80 for recommending an ECG filter to a user for use in the method 60 of FIG. 18 in accordance with one embodiment. First, a frequency of a recursive noise present in the ECG selection is identified (step 81). Second, one or more digital filters are selected based on the noise frequency (step 82). For example, if the selection includes high-frequency recursive noise, a low-pass filter can be chosen for the recommendation. Lastly, the selected filter is recommended to a user, terminating the routine 80 (step 83).

Figure 20:
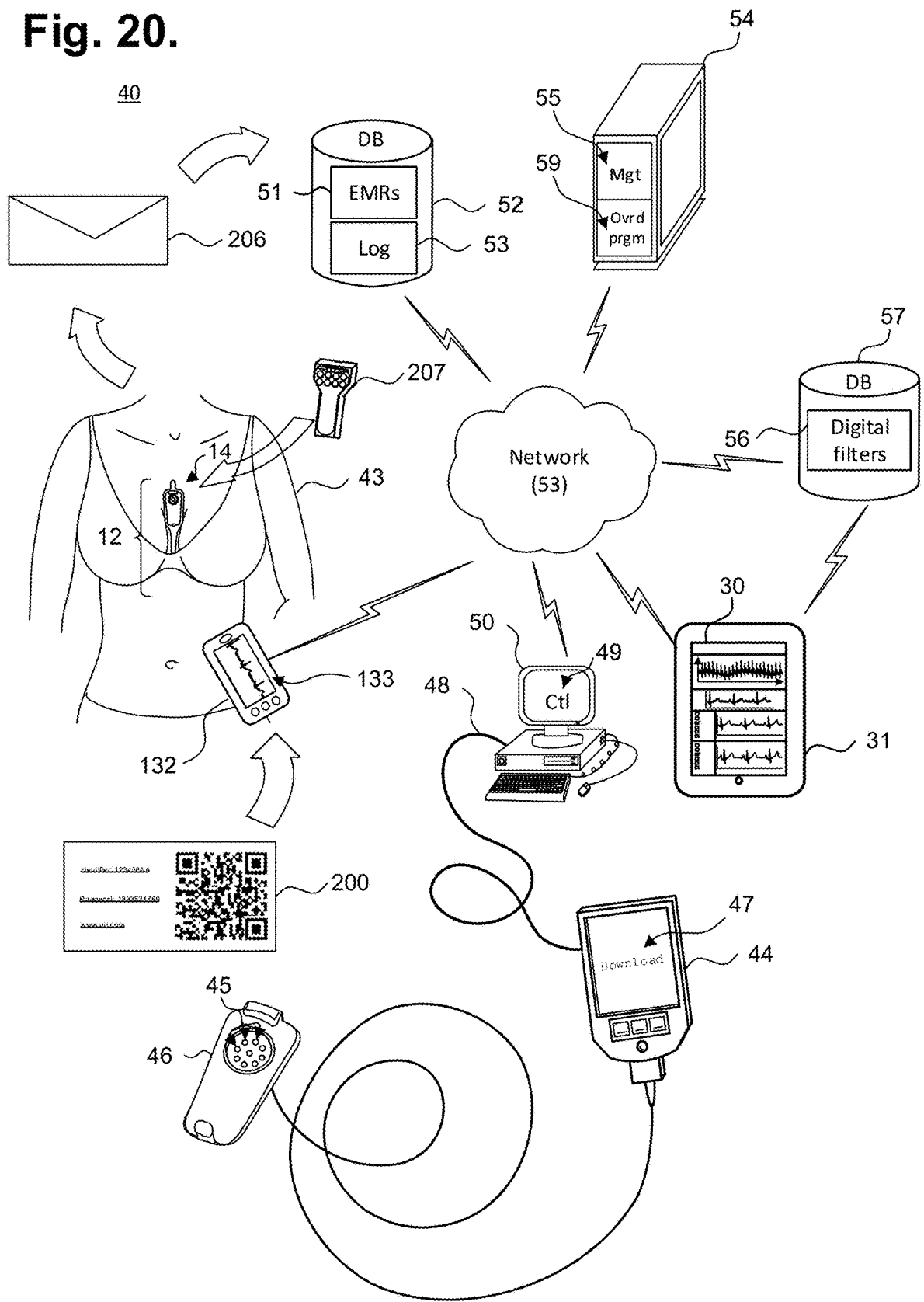
FIG. 20 is a functional block diagram showing a computer-implemented system for secure physiological data collection and processing in accordance with one embodiment.

The data obtained from the monitor 12, and optionally, filtered using the application 30, can be securely retrieved, stored, and accessed by the patient upon using the information on the label 200. FIG. 20 is a functional block diagram showing a computer-implemented system 40 for secure physiological data collection and processing in accordance with one embodiment.

The system 40 includes the monitor 12, which can offload data in a number of ways. Prior to being used to perform physiological monitoring, the recorder 14 and the patch 15 can be programmed using a programming wand 207. In particular, the wand 207 can generate the password 202 for an identifier 201 and load the identifier 201 and the password into the patch 15. In one embodiment, the wand can generate the identifier 201; in a further embodiment, the identifier 201 can be preloaded into the patch 15. The wand 207 also loads the secret key used to decode the password 202 into the monitor recorder 14. The wand 207 can interface with the recorder 14 and the patch 15 wirelessly, such as through the wireless transceivers 269 and 275. In a further embodiment, the wand 207 can interface with the recorder 14 and the patch 15 through wired connections. The wand 207 can include a wireless transceiver and can wirelessly interface with the server 54. For example, after loading an identifier 201 and the password 201 into the patch 15, the wand 207 can wirelessly send a report to the server 54 of what identifier 201 has been used and the password 202 generated for that identifier 202. The server 54 can keep track of whether data for the identifier has been received.

In one embodiment, the wand 207 can be used to program any number of patches 15 and recorders 14. In a further embodiment, the wand 207 can be configured to need recalibration after a preset number of uses.

As mentioned above, one of the options for offloading data from the monitor 12 can offload data to a download station 44. The monitor 12 has a set of electrical contacts (not shown) that enable the monitor recorder 14 to physically interface to a set of terminals 45 on a paired receptacle 46 of the download station 44. In turn, the download station 44 can execute a communications or offload program 47 ("Offload") or similar program that interacts with the monitor recorder 14 via the physical interface to retrieve the stored ECG monitoring data. When offloading the data off the monitor recorder, the identifier 201 and the decoded password 202 are included at the beginning of the stream of data that the monitor recorder 12 transfers to the download station 44. The download station 44 could be the user device 31 or another server, such as server 54, personal computer, tablet or handheld computer, smart mobile device, or purpose-built device designed specific to the task of interfacing with a monitor 12. Still other forms of download station 44 are possible. Also, as mentioned below, the data from the monitor 12 can be offloaded wirelessly.

Figure 21:
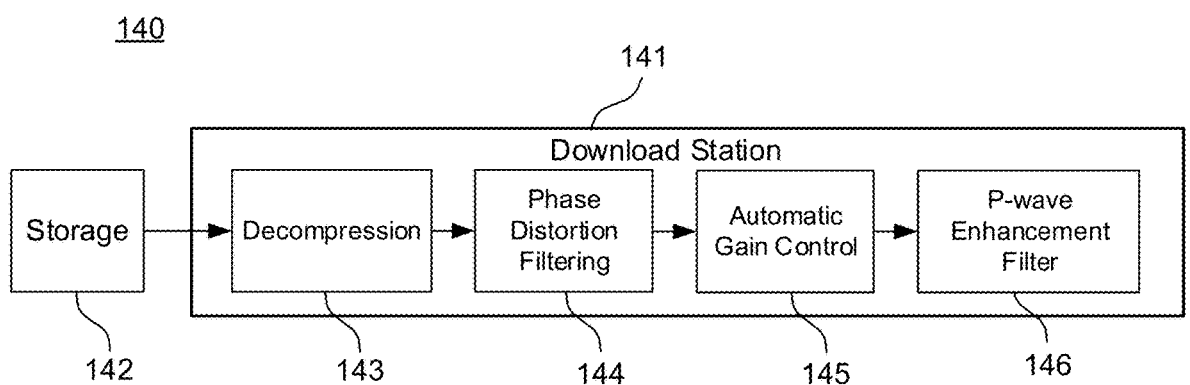
FIG. 21 is a functional block diagram showing operations performed by the download station in accordance with one embodiment.

The download station 44 can include an array of filtering modules that can perform processing of collected data instead of or in addition to the processing done using the application 30. For instance, a set of phase distortion filtering tools 144 may be provided as shown in FIG. 21. The digital signals are run through the software filters in a reverse direction to remove phase distortion. For instance, a 45 Hertz high pass filter in firmware may have a matching reverse 45 Hertz high pass filter in software. Most of the phase distortion is corrected, that is, canceled to eliminate noise at the set frequency, but data at other frequencies in the waveform remain unaltered. As well, bidirectional impulse infinite response (IIR) high pass filters and reverse direction (symmetric) IIR low pass filters can be provided. Data is run through these filters first in a forward direction, then in a reverse direction, which generates a square of the response and cancels out any phase distortion. This type of signal processing is particularly helpful with improving the display of the ST-segment by removing low frequency noise.

An automatic gain control (AGC) module 145 can also be provided to adjust the digital signals to a usable level based on peak or average signal level or other metric. AGC is particularly critical to single-lead ECG monitors, where physical factors, such as the tilt of the heart, can affect the electrical field generated. On three-lead Holter monitors, the leads are oriented in vertical, horizontal and diagonal directions. As a result, the horizontal and diagonal leads may be higher amplitude and ECG interpretation will be based on one or both of the higher amplitude leads. In contrast, the electrocardiography monitor 12 has only a single lead that is oriented in the vertical direction, so variations in amplitude will be wider than available with multi-lead monitors, which have alternate leads to fall back upon.

In addition, AGC may be necessary to maintain compatibility with existing ECG interpretation software, which is typically calibrated for multi-lead ECG monitors for viewing signals over a narrow range of amplitudes. Through the AGC module 145, the gain of signals recorded by the monitor recorder 14 of the electrocardiography monitor 12 can be attenuated up (or down) to work with FDA-approved commercially available ECG interpretation.

AGC can be implemented in a fixed fashion that is uniformly applied to all signals in an ECG recording, adjusted as appropriate on a recording-by-recording basis. Typically, a fixed AGC value is calculated based on how an ECG recording is received to preserve the amplitude relationship between the signals. Alternatively, AGC can be varied dynamically throughout an ECG recording, where signals in different segments of an ECG recording are amplified up (or down) by differing amounts of gain.

Typically, the monitor recorder 14 will record a high resolution, low frequency signal for the P-wave segment. However, for some patients, the result may still be a visually small signal. Although high resolution is present, the unaided eye will normally be unable to discern the P-wave segment. Therefore, gaining the signal is critical to visually depicting P-wave detail. This technique works most efficaciously with a raw signal with low noise and high resolution, as generated by the monitor recorder 14. Automatic gain control applied to a high noise signal will only exacerbate noise content and be self-defeating.

Finally, the download station 44 can include filtering modules specifically intended to enhance P-wave content. For instance, a P-wave enhancement filter 146, which is a form of pre-emphasis filter, can be applied to the signal to restore missing frequency content or to correct phase distortion. Still other filters and types of signal processing are possible.

Figure 22:
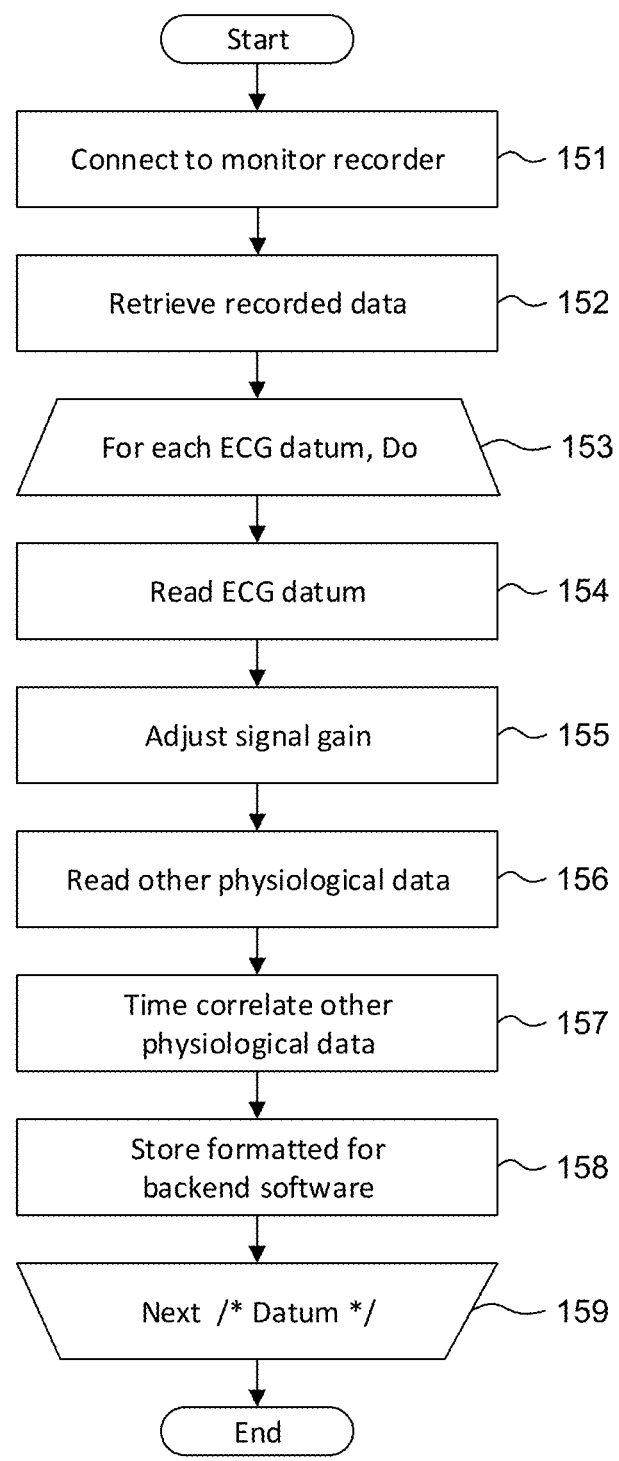
FIG. 22 is a flow diagram showing a method for offloading and converting ECG and other physiological data from an extended wear electrocardiography and physiological sensor monitor in accordance with one embodiment.

In addition to the processing described above, the download station 44 can also convert retrieved data into a format suitable for use by third party post-monitoring analysis software, such as the application 30, as further described below with reference to FIG. 22. If the download station 44 is not the user device 31, the formatted data can then be retrieved from the download station 44 over a hard link 48 using a control program 49 ("Ctl") or analogous application executing on a personal computer 50 or other connectable computing device, via a communications link (not shown), whether wired or wireless, or by physical transfer of storage media (not shown). The personal computer 50 or other connectable device may also execute middleware that converts ECG data and other information into a format suitable for use by a third-party post-monitoring processing program, such the application 30. Note that formatted data stored on the personal computer 50 would have to be maintained and safeguarded in the same manner as electronic medical records (EMRs) 51 in a secure database 52, as further discussed infra. In a further embodiment, the download station 44 is able to directly interface with other devices over a computer communications network 53, which could be some combination of a local area network and a wide area network, including the Internet, over a wired or wireless connection. Still other forms of download station 44 are possible. In addition, the wearable monitor 12 can interoperate with other devices, as further described in detail in commonly-assigned U.S. Pat. No. 9,433,367, issued Sep. 6, 2016, the disclosure of which is incorporated by reference. In addition, the wearable monitor 12 is capable of interoperating wirelessly with mobile devices 132, including so-called "smartphones," and can use the mobile devices 132 to relay collected data to other devices in the system 40, such as described in commonly-assigned U.S. Patent Application Publication No. 2015/0088007, published Mar. 26, 2015, the disclosure of which is incorporated by reference. Further, as mentioned above, the monitor 12 can include a wireless transceiver with a cellular phone capabilities, and in a further embodiment could connect directly to the network 53 and interact with other devices in the system 40, such as the server 54, the download station 44, and the mobile device 132 using the network 53.

A client-server model could be used to employ a server 54 to remotely interface with the download station 44 over the network 53 and retrieve the formatted data or other information. The server 54 executes a patient management program 55 ("Mgt") or similar application that stores the retrieved formatted data and other information in the secure database 52 cataloged in that patient's EMRs 51. The application 30 can receive the results of the monitoring from the server 54 if in possession of the identifier 201 and password 202. In addition, the patient management program 55 could manage a subscription service that authorizes a monitor recorder 12 to operate for a set period of time or under pre-defined operational parameters.

In a further embodiment, the download station 44 could be used to transfer data from the monitor 12 to the server 54 without involvement of the network 53. For example, following a completion of the monitoring, the patient 11 can use an envelope 206 to mail the monitor to a processing center (not shown), where information is extracted from the monitor 12 using the download station 44 directly connected to the server 54.

In a still further embodiment, the server 54 could receive the data collected by the monitor 12 directly from the monitor 12 over a wireless connection.

Upon receiving the data collected by the monitor 12, which includes data such as ECG data and other physiological data, the server 54 identifies the password 202 and the identifier 201 in the data.

The patient management program 55, or other trusted application executed by the server 54, also maintains and safeguards the secure database 52 to limit access to patient EMRs 51 to only authorized parties for appropriate medical or other uses, such as mandated by state or federal law, such as under the HIPAA or per the European Union's Data Protection Directive. For example, a physician may seek to review and evaluate his patient's ECG monitoring data, as securely stored in the secure database 52. In particular, the database stores a log 58 of identifiers 201 of the patches 15 that have been issued and the passwords 202 that are associated with the patches 15 with the identifiers. Once the server receives the data from the monitor 12, the server compares the identifiers 201 and passwords 202 stored in the log 58 with the identifiers and passwords 203 included in the data received from the monitor 12. If the identifiers 201 and passwords 202 match, the server 54 stores the physiological data, such as ECG data, collected by the monitor as EMRs 51 associated with a particular identifier 201.

The EMRs 51 are not associated with and the database 52 does not store any patient identifying information, but are instead stored under the identifier 201 of the patch 15 used to collect data in the EMRs. By excluding the patient identifying information and organizing the EMRs 51 exclusively based on the identifiers 201, the database 52 the database eliminates the risk of violating particular laws regarding disclosure of patient identifying information since such information is not stored. In a further embodiment, the database 52 can store information needed to contact the patient or another authorized party, such as the phone number of the patient's doctor.

As mentioned above, the monitor 12 can collect multiple kinds of physiological data and thus the EMRs 51 can include diverse physiological data such as samples of the electrocardiographic data, and data from other sensors of the monitor 12, such as air-flow data, actigraphy data, temperature data, though other kinds of data is possible. Further, the server 54 can receive a filtered ECG trace processed using the application 30 on a user device and store the trace with the EMR 51 associated with the identifier 201 of the patch used to collect the ECG samples on which the trace is based.

Further, the server 54 can also implement an automated over-read program 59 that conducts an automated over-read of the ECG trace generated based on the data obtained by the monitor 12. Prior to the over-read, the trace can be filtered using the software 30. In a further embodiment, the trace can undergo other kinds of processing prior to being subject to the over-read. During the over-read, the program 59 compares features of the ECG trace, such as shape and position of the waves, to ECG trace features known to be indicative of one or more conditions. For example, irregular distances between successive R waves ("R-to-R intervals") in an ECG can be indicative of atrial fibrillation, one of the most common cardiac arrhythmias that is caused by seemingly disorganized atrial depolarizations without effective atrial contractions. By analyzing the R-to-R intervals in the ECG trace created based on the electrocardiographic signals collected by the monitor, the program 59 can detect a presence of a condition indicative of atrial fibrillation. Further, in addition to detecting of ECG characteristics indicative of the condition, the program 59 can generate a recommendation based on the detected condition. The recommendation and other results of the over-read can be stored as part of the EMRs 51 associated with the identifier 201 for the patch 15 that was used to collect the physiological data used in the over-read. In a further embodiment, the recommendation can be provided to the patient 10, 11 or another authorized party as an alert.

The recommendation can depend on the duration of the detected condition. For example, if the analysis of the R-R waves indicates that the patient 10, 11 has been experiencing atrial fibrillation for more than an hour, the recommendation can be for the patient to take a dose of an appropriate medication, such as aspirin. Similarly, as prolonged atrial fibrillation can increase a risk of stroke, if the analysis of the R-R waves indicates that the patient has been experiencing atrial fibrillation for more a day or more, the recommendation can include visiting a physician for elective cardioversion prior to the likely development of an atrial clot. Other kinds of indications are possible. Still other data can be part of the EMRs 51.

The server 51 further maintains a website 133 where the patient 10, 11 or another authorized party can access the patient's EMRs. For example, the patient can use the mobile device 132 to scan the QR code 204, with the EMRs corresponding to the supplied identifier being presented on a webpage that is a part of the website 133 through the mobile device 132. As mentioned above, the QR code 32 could be scanned using a separate scanner, such as a scanner (not shown) attached to the computer 50, with the website being presented through the computer 50. Other devices can also be used to access the website 133.

The monitor recorder 14 stores ECG data and other information in the flash memory 262 (shown in FIG. 9) using a proprietary format that includes data compression. As a result, data retrieved from a monitor recorder 14 must first be converted into a format suitable for use by third party post-monitoring analysis software. FIG. 22 is a flow diagram showing a method 150 for offloading and converting ECG and other physiological data from a extended wear electrocardiography and physiological sensor monitor 12 in accordance with one embodiment. The method 150 can be implemented in software and execution of the software can be performed on a download station 44, which could be a programmer or other device, or a computer system, including a server 54 or personal computer 50, such as further described supra with reference to FIG. 20, as a series of process or method modules or steps. For convenience, the method 150 will be described in the context of being performed by a personal computer 50 or other connectable computing device (shown in FIG. 3) as middleware that converts ECG data and other information into a format suitable for use by a third-party post-monitoring analysis program. Execution of the method 150 by a computer system would be analogous mutatis *mutandis*.

Initially, the download station 44 is connected to the monitor recorder 14 (step 151), such as by physically interfacing to a set of terminals 45 on a paired receptacle 127 or by wireless connection, if available. The data stored on the monitor recorder 14, including ECG and physiological monitoring data, other recorded data, and other information are retrieved (step 152) over a hard link 48 using a control program 49 ("Ctl") or analogous application executing on a personal computer 50 or other connectable computing device.

The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 153-159) in an iterative processing loop. During each iteration (step 153), the ECG datum is read (step 154) and, if necessary, the gain of the ECG signal is adjusted (step 155) to compensate, for instance, for relocation or replacement of the electrode patch 15 during the monitoring period. Filtering described below with reference to FIG. 21 can also optionally take place during step 155.

In addition, depending upon the configuration of the wearable monitor 12, other physiological data (or other information), including patient events, such as a fall, peak activity level, sleep detection, detection of patient activity levels and states, and so on, may be recorded along with the ECG monitoring data. For instance, actigraphy data may have been sampled by the actigraphy sensor 264 based on a sensed event occurrence, such as a sudden change in orientation due to the patient taking a fall. In response, the monitor recorder 14 will embed the actigraphy data samples into the stream of data, including ECG monitoring data, that is recorded to the flash memory 262 by the microcontroller 261. Post-monitoring, the actigraphy data is temporally matched to the ECG data to provide the proper physiological context to the sensed event occurrence. As a result, the three-axis actigraphy signal is turned into an actionable event occurrence that is provided, through conversion by the middleware, to third party post-monitoring analysis programs, along with the ECG recordings contemporaneous to the event occurrence. Other types of processing of the other physiological data (or other information) are possible.

Thus, during execution of the middleware, any other physiological data (or other information) that has been embedded into the recorded ECG monitoring data is read (step 156) and time-correlated to the time frame of the ECG signals that occurred at the time that the other physiological data (or other information) was noted (step 157). Finally, the ECG datum, signal gain adjusted, if appropriate, and other physiological data, if applicable and as time-correlated, are stored in a format suitable to the backend software (step 158) used in post-monitoring analysis.

In a further embodiment, the other physiological data, if apropos, is embedded within an unused ECG track. For example, the SCP-ENG standard allows multiple ECG channels to be recorded into a single ECG record. The monitor recorder 14, though, only senses one ECG channel. The other physiological data can be stored into an additional ECG channel, which would otherwise be zero-padded or altogether omitted. The backend software would then be able to read the other physiological data in context with the single channel of ECG monitoring data recorded by the monitor recorder 14, provided the backend software implemented changes necessary to interpret the other physiological data. Still other forms of embedding of the other physiological data with formatted ECG monitoring data, or of providing the other physiological data in a separate manner, are possible.

Processing continues (step 159) for each remaining ECG datum, after which the processing loop is exited and execution terminates. Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. A system for secure physiological data acquisition and delivery, comprising:
 a monitoring patch, comprising:
  a flexible backing comprising stretchable material defined as an elongated strip with a narrow longitudinal midsection;
  a pair of electrocardiographic electrodes comprised on a contact surface of each end of the flexible backing, each electrocardiographic electrode conductively exposed for dermal adhesion and adapted to be positioned axially along a midline of a sternum for capturing action potential propagation;
  a receptacle affixed to a non-contacting surface of the flexible backing and comprising an electro-mechanical docking interface for interfacing with a monitor recorder;
  a pair of flexible circuit traces affixed at each end of the flexible backing with each circuit trace connecting one of the electrocardiographic electrodes to the electro-mechanical docking interface; and
  a circuit operable to store an identifier associated with the patch and an encrypted password necessary to access physiological monitoring data obtained using the patch identified by that identifier, the circuit configured to provide via the electro-mechanical docking interface the password and the identifier to the monitor recorder.

2. A system according to claim 1, wherein the password and the identifier are provided to the monitor recorder prior to a beginning of a collection of electrocardiographic data by the monitor recorder using the pair of the electrocardiographic electrodes.

3. A system according to claim 2, further comprising:
 the circuit configured to perform an authentication procedure with the monitor recorder prior to providing the identifier and the password to the monitor recorder.

4. A system according to claim 1, wherein the password is encrypted using the secret key and the monitor recorder is in possession of the secret key.

5. A system according to claim 1, wherein the password is a cryptographic hash of at least a portion of the identifier.

6. A system according to claim 1, the monitoring patch further comprising:
 a wireless transceiver configured to receive the encrypted password from a programming wand.

7. A system according to claim 1, further comprising:
 a wireless transceiver comprised in one of the monitoring patch and the monitor recorder and configured to offload physiological data collected using the monitoring patch together with the password and the identifier.

8. A system according to claim 7, further comprising:
 a mobile device configured to receive the offloaded physiological data together with the password and the identifier and to relay the physiological data, the password, and the identifier over a communication network to a server, which processes the physiological data using the identifier and the password.

9. A system according to claim 7, the monitoring patch further comprising a physiological sensor, wherein data collected by the physiological sensor is provided to the monitor recorder via the electro-mechanical docking interface.

10. A system according to claim 1, the monitoring patch further comprising:
 a battery interfaced to the electro mechanical docking interface and configured to power the monitor recorder via the docking interface and the circuit.

11. A multipart system for secure physiological data acquisition and delivery, comprising:
 a monitoring patch, comprising:
  a flexible backing comprising stretchable material defined as an elongated strip;
  a pair of electrocardiographic electrodes comprised on a contact surface of each end of the flexible backing, each electrocardiographic electrode conductively exposed for dermal adhesion and adapted to be positioned axially along a midline of a sternum for capturing action potential propagation;
  a receptacle affixed to a non-contacting surface of the flexible backing and comprising an electro-mechanical docking interface for interfacing with a monitor recorder, the electro-mechanical docking interface comprising a plurality of electrical contact mating pads;
  a pair of flexible circuit traces affixed at each end of the flexible backing with each circuit trace connecting one of the electrocardiographic electrodes to two of the electrical contact mating pads of the electro-mechanical docking interface; and
  a circuit operable to store an identifier associated with the patch and an encrypted password necessary to access physiological monitoring data obtained using the patch identified by that identifier, the circuit configured to provide via at the electro-mechanical docking interface the password and the identifier to the monitor recorder.

12. A system according to claim 11, wherein the password and the identifier are provided to the monitor recorder prior to a beginning of a collection of electrocardiographic data by the monitor recorder using the pair of the electrocardiographic electrodes.

13. A system according to claim 12, further comprising:
 the circuit configured to perform an authentication procedure with the monitor recorder prior to providing the identifier and the password to the monitor recorder.

14. A system according to claim 11, wherein the password is encrypted using the secret key and the monitor recorder is in possession of the secret key.

15. A system according to claim 11, wherein the password is a cryptographic hash of at least a portion of the identifier.

16. A system according to claim 11, the monitoring patch further comprising:
 a wireless transceiver configured to receive the encrypted password from a programming wand.

17. A system according to claim 11, further comprising:
 a wireless transceiver comprised in one of the monitoring patch and the monitor recorder and configured to offload physiological data collected using the monitoring patch together with the password and the identifier.

18. A system according to claim 17, further comprising:
 a mobile device configured to receive the offloaded physiological data together with the password and the identifier and to relay the physiological data, the password, and the identifier over a communication network to a server, which processes the physiological data using the identifier and the password.

19. A system according to claim 17, the monitoring patch further comprising a physiological sensor, wherein data collected by the physiological sensor is provided to the monitor recorder via the electro-mechanical docking interface.

20. A system according to claim 11, the monitoring patch further comprising:
 a battery interfaced to the electro mechanical docking interface and configured to power the monitor recorder via the docking interface and the circuit.

\* \* \* \* \*